United States Patent
Merlini et al.

(10) Patent No.: US 8,101,793 B2
(45) Date of Patent: *Jan. 24, 2012

(54) RETINOID DERIVATIVES WITH ANTIANGIOGENIC, ANTITUMORAL AND PROAPOPTOTIC ACTIVITIES

(75) Inventors: Lucio Merlini, Milan (IT); Sabrina Dallavalle, Milan (IT); Sergio Penco, Milan (IT); Giuseppe Giannini, Rome (IT); Claudio Pisano, Rome (IT); Loredana Vesci, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 2089 days.

This patent is subject to a terminal disclaimer.

(21) Appl. No.: 10/485,530

(22) PCT Filed: Jul. 18, 2002

(86) PCT No.: PCT/IT02/00474
§ 371 (c)(1),
(2), (4) Date: Feb. 2, 2004

(87) PCT Pub. No.: WO03/011808
PCT Pub. Date: Feb. 13, 2003

(65) Prior Publication Data
US 2004/0235757 A1  Nov. 25, 2004

(30) Foreign Application Priority Data
Jul. 31, 2001   (IT) .............................. RM2001A0464

(51) Int. Cl.
C07C 62/32 (2006.01)
C07C 69/618 (2006.01)
C07C 59/72 (2006.01)
C07D 317/50 (2006.01)
A61P 35/00 (2006.01)
A61P 35/02 (2006.01)
A61P 35/04 (2006.01)
A61K 31/195 (2006.01)
A61K 31/192 (2006.01)
A61K 31/222 (2006.01)
A61K 31/36 (2006.01)

(52) U.S. Cl. ........ 562/467; 562/478; 562/466; 562/474; 562/475; 562/492

(58) Field of Classification Search ................. 562/400, 562/405, 433, 465, 469, 470; 514/784, 785, 514/476, 579, 715, 716, 717, 718
See application file for complete search history.

(56) References Cited

U.S. PATENT DOCUMENTS 5,547,983 A * 8/1996 Charpentier .................. 514/535
7,053,071 B2 * 5/2006 Dawson et al. ................. 514/92
7,449,495 B2 * 11/2008 Dallavalle et al. ............ 514/720

OTHER PUBLICATIONS

Tittley et al. J. Med. Chem. 1989, 32, 1814-1820.*
RN 146966-12-3 CAPLUS.*
RN 14966-12-3 entered 1996.*
Database Crossfire Beilstein 'Online! Beilstein Institute zur Forderung der chemischen Wissenschaften, Frankfurt am Main, DE; Database accession No. 3358409; 3350893 XP002222169 abstract & Mudrovcic: Monatsh. Chem., vol. 34, 1913, p. 1428.
Database Crossfire Beilstein 'Online! Beilstein Institute zur Forderung der chemischen Wissenschaften, Frankfurt am Main, DE; Database accession No. 7997805 XP002222170 abstract & Krestinina, T.B.: Russ. J. Org. Chem., vol. 33, No. 7, 1997, pp. 1044-1045.
Database Crossfire Beilstein 'Online! Beilstein Institute zur Forderung der chemischen Wissenschaften, Frankfurt am Main, DE; Database accession No. 2663218 XP002222171 abstract & Rabiloud, G. et al: Bull. Soc Chem. FR., 1977, pp. 281-287.
Jefferson W. Tilley et al: "Biphenylcarboxamide Derivatives as Antagonists of Platelet-Activating Factor" J. Med. Chem., vol. 32, No. 8, 1989, pp. 1814-1820, XP002222168 *compounds 12 and 8c*.
Charpenter B et al: "Synthesis, Structure-Affinity Relationships, and Biological Activities of Ligands Binding to Retinoic Acid Receptor Subtypes" Journal of Medicinal Chemistry, American Chemical Society. Washington, US, vol. 38, No. 26, 1995, pp. 4993-5006, XP000971461 ISSN:0022-2623 cited in the application *scheme 1-9* abstract.
Zhang et al., Blood (2002) vol. 100, No. 8, p. 2917-2925.

* cited by examiner

Primary Examiner — Daniel Sullivan
Assistant Examiner — Yevegeny Valenrod
(74) Attorney, Agent, or Firm — Vedder Price P.C.; Thomas J. Kowalski; Deborah L. Lu

(57) ABSTRACT

Are described compounds of Formula (I) in which R, R', R", A, and D have the meanings described in the text, as useful agents in the cure of pathologies characterized by altered angiogenesis and as antitumorals.

25 Claims, 2 Drawing Sheets

Figure 1:
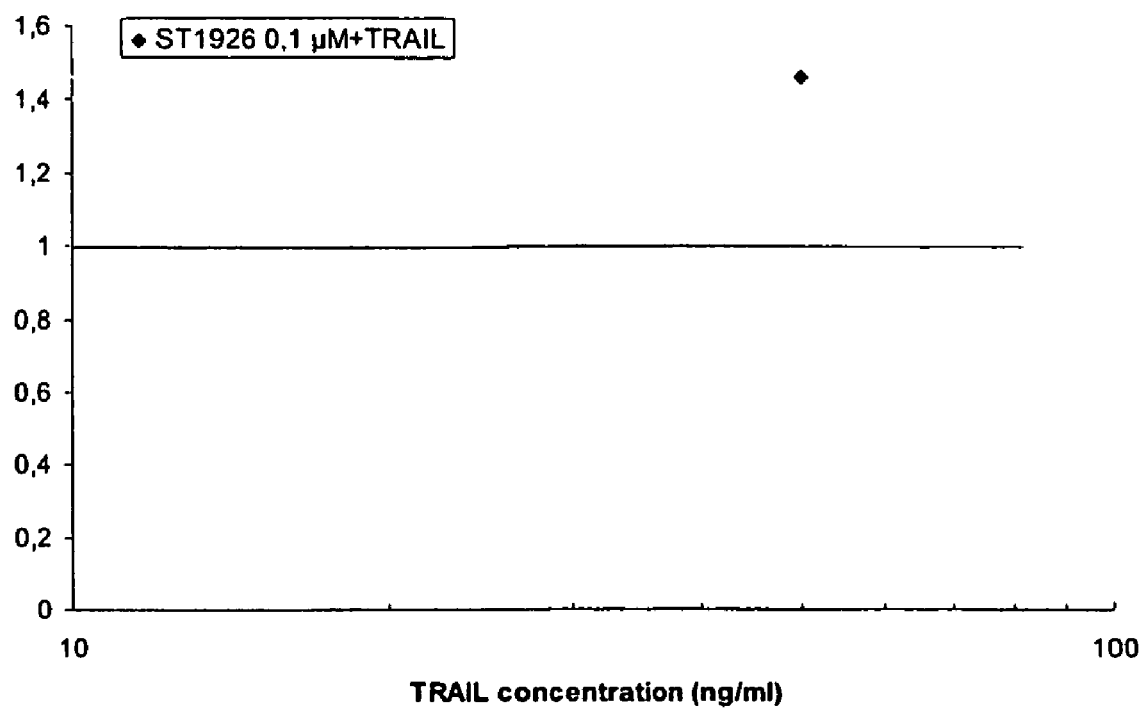

RETINOID DERIVATIVES WITH ANTIANGIOGENIC, ANTITUMORAL AND PROAPOPTOTIC ACTIVITIES

This application is the US national phase of international application PCT/IT02/00474, filed in English on 18 Jul. 2002, which designated the U.S. PCT/IT02/00474 claims priority to IT Application No. RM2001A000464 filed 31 Jul. 2001. The entire contents of these applications are incorporated herein by reference.

The present invention relates to retinoid derivatives, endowed with antitumoural antiangiogenic, pro-apoptotic anti-inflammatory activity, having general Formula (I):

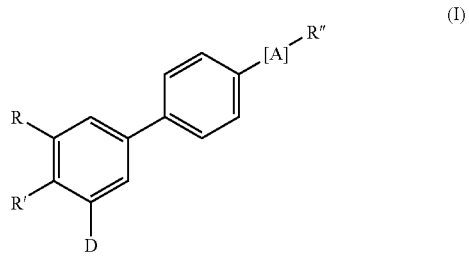

wherein:

R represents alkyl, cycloalkyl, heterocycloalkyl, phenyl, phenyl substituted, adamantyl wherein at least one of the CH can be substituted with C-halogen or C-alkyl and one of the $CH_2$ can be substituted by O, S, CH-halogen, CH-aryl, CH-heteroaryl, CH-arylalkyl, CH-heteroarylalkyl, CH-amino;

R' represents OR''', OCOR''', $COR^{IV}$;

R'-D represents O—$(CH_2)$n-O; where n=1-3;

D represents H, OH, O-alkyl, $(CH_2)$n-$NH_2$, $(CH_2)$n-NH-alkyl, $(CH_2)$n-OH, where n=1-4;

R'' represents tetrazole, $SO_3H$, $NHSO_3H$, CHO, COOH, COO-alkyl, CONHOH, CONH-aryl, CONH—$C_6H_4OH$, $CH_2OR'''$; $PO_3H_2$; CO—$(CH_2)$n-aryl, where n=0-4;

R''' represents H, alkyl, aryl, arylalkyl, heteroaryl, heteroarylalkyl, $SO_3H$, α or β D- and L-glycosyl;

$R^{IV}$ represents H, OH, OR''';

[A] represents $[C(R^V,R^{VI})—C(R^{VII},R^{VIII})]n$, $[C(R^{IX})=C(R^X)]n$, $[C≡C]n$, where n=0-3;

$R^V$, $R^{VI}$, $R^{VII}$, $R^{VIII}$ represent H, alkyl, halogen, OH, OR''', $NO_2$, $NH_2$, aryl, —O—, —$CH_2$—, $CX_2$— (where X is halogen), —CH(R''')—; $R^{IX}$, $R^X$ represent H, OH, halogen, alkyl, aryl, CN, $NO_2$, COOR'''.

Vitamin A and its biologically active derivatives, retinal and retinoic acid, play an important role in vision, are necessary in the reproductive system, act as morphogenic agents during embryonic growth and regulate the growth and differentiation of a vast range of cell types at the basis of the growth of an organism [M. Sporn, A. Roberts, D. Goodman, *The Retinoids*, Raven Press, New York 1994]. The biological action of retinoic acid and its derivatives is mediated by the interaction with nuclear receptors belonging to two families: the first named RAR (retinoic acid receptor) and the second named RXR (retinoid X receptor) [P. Chambon, *FASEB J.*, 1996, 10, 940-54]. Each family is divided into 3 subtypes (α, β, γ) coded by three different genes.

All-Trans-Retinoic Acid (ATRA) binds to RAR and RXR, whilst 9-cis RA binds only to RXR.

Retinoids, whether natural or synthetic vitamin A analogues, exercise a great influence over cellular proliferation, differentiation and apoptosis: these properties are amply exploited in the control of tumoral and dermatological pathologies, and pathologies linked to an altered angiogenesis.

Angiogenesis in the adult is normally quiescent, but it represents a normal function, for example in the healing of wounds, or in the reconstruction of the endometrium during the female reproductive cycle.

The angiogenic response is physiologically stimulated when the vascular functions are reduced and tissue perfusion is inadequate.

More generally, it can be claimed that, in physiological conditions, angiogenesis constitutes a positive feedback in response to inadequate perfusion, or to a reduced supply of oxygen and nutrients, such as occurs, for instance, in the case of occlusion of an artery, in situations of tissue mass growth (for example, the neovascularisation that accompanies the formation of muscle tissue); and in the case of an increased work load in association with an increased oxygen and nutrient requirement.

In the course of local ischaemia, due to partial or complete occlusion of an artery, the development of collateral vessels is necessary in order to maintain perfusion.

It is well known that the growth of a primary tumour is favoured by good vascularization of the tumour tissue. An adequate supply of oxygen and nutrients promotes rapid growth of the tumour itself.

It has been demonstrated that the extent of angiogenesis can be an extremely negative factor in the prognosis of neoplasms (van Hinsbergh V W, Collen A, Koolwijk P; *Ann. Oncol.*, 10 Suppl., 4:60-3, 1999; Buolamwini J K; *Curr., Opin., Chem., Biol.*, 3(4):500-9, August 1999).

It is also known, that a fundamental stage in the biology of the tumour cell is the acquisition of metastasising capability.

The tumour cells that metastasise are able to lose adherence to the surrounding structures, invade blood and lymphatic vessels and colonise other tissues at a distance where they can continue to reproduce themselves.

Metastasis is also a critical event in the clinical history of the disease, being the main cause of death due to cancer. It is closed associated with and facilitated by the presence of vascular tissue in the tumour site or adjacent areas.

The migration of tumour cells across the surrounding structures enables the cells to reach the intratumoural blood vessels, whether pre-existing or formed by neo-angiogenesis, and thus reach the bloodstream (Ray J M., Stetler-Stevenson W G; *Eur. Respir. J.*, 7(11):2062-72, 1994; Stetler-Stevenson W G, Liotta L A, Kleiner D E Jr; *FASEB J.*, 7(15):1434-41, December 1993).

The presence of communication between lymphatic and blood vessels in the vascular region of the tumour enables the neoplastic cells to move in both vascular systems.

Recent studies have shown a direct relationship between angiogenesis and arthritic disease (Koch A E; *Arthritis and Rheumatism* 41:951-962, 1998). In particular, it has been demonstrated that neo-vascularization of the articular cartilages plays a crucial role in pannus formation and in progression of arthritis. A normal cartilage does not possess blood vessels, while the synovial fluid of arthritic patients contains an angiogenesis-stimulating factor produced by endothelial cells (EASF).

The presence of this factor is associated with vascularization and degradation of the cartilage.

Other diseases are also related to abnormal angiogenesis.

It has been -found that, in diabetic retinopathy [*Histol Histopathol* October 1999; 14(4):1287-94], psoriasis [*Br. J. Dermatol.* December 1999; 141(6):1054-60], chronic inflammation and atherosclerosis [*Planta Med.* December 1998; 64(8):686-95], neovascularisation of the affected tissues is a facilitating factor.

The control of neovascularisation is therefore one of the basic elements for the control and cure of these diseases.

Retinoids useful for treating cancer or having antiangiogenic activity are already known.

A compound belonging to the last generation of retinoids, CD437 (*Cancer Research*, 2002; 62(8), 2430-6; *Blood*, 2000; 95, 2672-82; *Leukemia*, 1999, 13, 739-49; *Cancer Letters*, 1999, 137, 217-2) is selective for RARγ, inhibits cell growth and induces apoptosis in breast carcinoma, melanoma and cervical carcinoma cell lines, including those ATRA-resistant, with a mechanism independent receptor binding (WO9703682; *J.Med.Chem.* 1995, 38, 4993-5006). Both CD437 and other derivatives such as the cis-TTNPB derivative (ac. Tetramethyl-Tetrahydro-Naphthalenyl-Propenyl Benzoate), act as leads for the development of new apoptosis inducing agents In parallel, some retinoids, obtained through synthesis, such as TAC-101 [*Clin.Cancer Res.* 1999, 5,2304-10] or derivatives such as RE-80, AM-580 or Am-80 [*Eur.J.Pharmacol.* 1993, 249, 113-6] have shown antiangiogenic properties.

Despite the progress made in recent years, the pharmacological research concerned with discovering new drugs for the treatment of tumor diseases and diseases characterised by abnormal angiogenesis is still considered by many experts in medicine as one of the most promising field.

In fact, to date there is still a strongly perceived need for new compounds capable of blocking or interfering with the tumour diseases and diseases caused by abnormal angiogenesis. As mentioned above, these diseases include tumours, tumours metastasis, chronic inflammation, arthritic diseases, diabetic retinopathy, psoriasis, chronic inflammation and atherosclerosis.

It has now been surprisingly found that compounds having general Formula (I) are endowed with antitumour, pro-apoptotic, and antiangiogenic activity.

The compounds of Formula (I), according to the present invention were never described before.

Compounds with general formula (I) are therefore the object of the invention described herein.

A further object of the invention described herein are compounds with general formula (I) and their use in the medical field.

A further object of the invention described herein are compounds with general formula (I) and a process for their preparation.

A further object of the invention described herein is a pharmaceutical composition containing as active ingredient a formula (I) compound and at least a pharmaceutically acceptable excipient and/or diluent.

A further object of the present invention relates to the use of a compound of formula (I) for the preparation of a medicament for the treatment of pathologies related to altered angiogenesis, in which the pathology is selected in the group comprising arthritic pathology, tumours, metastatisation, diabetic retinopathy, psoriasis, chronic inflammatory disease, and atherosclerosis.

A further object of the present invention relates to the use of a compound of formula (I) for the preparation of a medicament for the treatment of tumours, wherein the antitumoral activity is of cytotoxic nature, and/or apoptotic nature, and/or antiangiogenic nature; wherein the tumour is selected from the group comprising sarcoma, carcinoma, carcinoid, bone tumour, neuroendocrine tumour, lymphoid leukaemia, myeloid leukaemia, monocytic leukaemia, megakaryocytic leukaemia, acute promyelocytic leukaemia or Hodgkin's disease.

A further object of the present invention relates to the use of a compound of formula (I), for the preparation of a medicament useful for the prevention and treatment of tumour metastasis.

As mentioned above, the growth of a primary tumour is facilitated by good vascularization of the tumour tissue, and the extent of the neoangiogenesis may be a highly adverse factor in the prognosis of neoplasms. An adequate supply of oxygen and nutrients in the tumour site, in fact, facilitates rapid growth of the tumour itself.

It is well known that the antitumour agents available to physicians for the treatment of tumours are still unable to prevent many patients from dying of these diseases. It is also well known that most oncological patients are treated not with a single anticancer drug but with a combination of several anticancer agents. The need to administer anticancer drugs in combination stems from the fact that by acting at different metabolic levels in some cases they favour complete remission of the tumour, while in others they lengthen the patient's life, and/or improve the quality of life of the treated patients.

To date there is still a strongly perceived need for new compounds to be used in combination with known antitumour compounds.

The compound according to the invention described herein can be used in combination with one or more anticancer drugs.

A further object of the invention described herein is the combination of one or more compound of formula (I) with one or more known anticancer drugs, in which the anticancer drug is selected from the group comprising alkylating agents, topoisomerase inhibitors, antitubulin agents, intercalating compounds, anti-metabolites, natural products such as vinca alkaloids, epipodophyllotoxins, antibiotics, enzymes, taxans, cyto-differentiating compounds, phosphotyrosine kinase inhibitors such as Iressa or Glivec, TRAIL (tumor necrosis factor-related apoptosis inducing ligand), agonists of DR4 or DR5 receptors (sites of TRAIL), compounds for immulogical antitumoral therapy, antitumoral vaccines, or interferon α, β, γ.

A further object of the invention described herein is a pharmaceutical composition comprising the combination of one or more compounds of formula (I) with one or more known anticancer drugs, and one or more excipients or vehicles pharmacologically acceptable.

A further object of the invention described herein is the use of one or more compound of Formula (I) with one or more known anticancer drugs, to prepare a medicament for the treatment of tumour.

A further object of the invention described herein is the use of one or more compound of Formula (I) with one or more known anticancer drugs, to prepare a medicament for the treatment of tumour, characterised in that the compound of formula (I) is present as coadjuvant of the anticancer drug.

The following examples illustrate the invention.

General Synthesis Procedure

Compounds of Formula (I) were prepared by reacting a compound of formula (II)

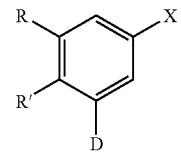

(II)

wherein R, R' and D have the meaning described in Formula (I) and X represents halogen, with 4-formylboronic acid in a Miyaura-Suzuki reaction (*Chem. Rev.* 1995, 95, 2457-83) to give an aldehyde of Formula (III).

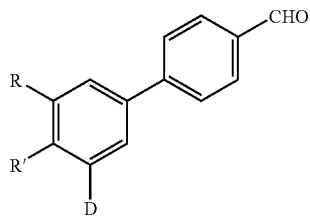

Compounds of formula (III), wherein R, R' and D have the meanings previously described, are made to react according to well known procedures described in the literature [e.g. reactions by Wittig (*Org. Reactions*, Vol.14), Wadsworth-Horner-Emmons (*Org. Reactions*, Vol.25), Knoevenagel (*Org. Reactions*, Vol.15), Henry (*Houben-Weyl, Methoden der organischen Chemie*, Vol. 10/1, p. 250), Darzens (*Org. Reactions*, Vol.5), etc.] to give compounds of general Formula (I), wherein [A] represents $C(R^V,R^{VI})=C(R^{VII},R^{VIII})$ and $R^V,R^{VI},R^{VII},R^{VIII}$ represent H, alkyl, halogen, OH, OR''', $NO_2$, $NH_2$, aryl, —O—, or where [A] represents C≡C.

Alternatively, compounds of general Formula (I) can be prepared from compounds of general Formula (II) through the reaction according to Miyaura-Suzuki (*Chem. Rev.* 1995. 95, 2457-83) with a boronic acid with general Formula (IV)

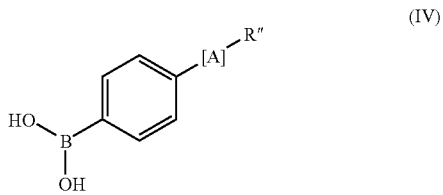

wherein A and R" have the meaning previously described.

Alternatively, the compounds of general Formula (I), where [A] represents $C(R^V,R^{VI})=C(R^{VII},R^{VIII})$ or C≡C can be prepared starting from compounds of general Formula (V)

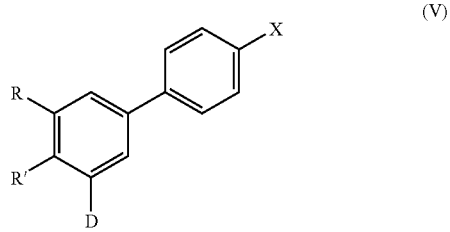

wherein R, R' and D have the meanings previously described, X represents halogen, through known methods, for example through reactions described by Heck (*Org. Reactions*, Vol.27) with alkenes or alkynes substituted in the presence of metal or organometallic catalysts.

Alternatively, compounds of general Formula (I), where [A] represents $C(R^V,R^{VI})=C(R^{VII},R^{VIII})$ or C≡C can be prepared starting from compounds of general Formula (I), in which R and D are H and R' has the meaning previously described, through alkylation reactions with alcohols, e.g. adamantan-1-ol, 1-methyl-1-cyclohexanol, tert-butanol, etc.

in the presence of sulphuric acid or other acids as catalysts, e.g. as described by Charpentier et al. (*J.Med.Chem.* 1995, 38, 4993-5006). With analogous reactions and the appropriate alcohols compounds of general Formula (I) can be prepared, starting from compounds of general Formula (I), where D is H and R, R' have the meanings previously described.

Compounds of general Formula (I) wherein [A] represents $C(R^V,H)$—$C(H,R^{VIII})$ and $R^V,R^{VIII}$ represents —$CH_2$—, can be prepared from compounds of general Formula (I) wherein [A] represents $C(R^V,R^{VI})=C(R^{VII},R^{VIII})$ through cyclopropanation reactions known in literature, e.g. reaction described by Simmons-Smith and analogues, as described for example in *J.Am.Chem.Soc.* 1959, 81, 4256 or in *J. Am. Chem. Soc.* 1981, 103, 5813, or from compounds of general Formula (I), wherein A is CH=$CH_2$, and R" is H, by reaction with ethyl diazoacetate. Compounds of general Formula (I), wherein [A] represents $C(R^V,H)$-$C(H,R^{VIII})$ and $R^V,R^{VIII}$ represents —O, can be prepared from compounds of general Formula (I) wherein [A] represents $C(R^V,R^{VI})=C(R^{VII},R^{VIII})$, through epoxidation reactions known in literature, for example with dioxirane or analogues, as described by Yang and colleagues. in *J. Org. Chem.*, 1995, 60, 3887-9.

Compounds of general Formula (I) wherein [A] represents C—C can be prepared from compounds of general Formula (I) wherein [A] represents $C(R^V,R^{VI})=C(R^{VII},R^{VIII})$ or C≡C through known reduction reactions for the double or triple bonds, for example catalytic hydrogenation.

Compounds of general Formula (I) wherein R" represents CONHOH can be prepared starting from compounds of general Formula (I) wherein R" represents COOH through procedures known in literature for the synthesis of hydroxamic acids, for example through reaction with O-benzylhydroxylamine and condensating agents, [De Luca et al. *J.Org.Chem.*, 2001, 66, 25341] followed by catalytic hydrogenation, or with O-trimethylsilylhydroxylamine followed by desilylation.

Compounds of general Formula (I) wherein R" represents CONHaryl can be prepared from compounds of general Formula (I) wherein R" represents COOH through procedures known in literature for the synthesis of amides, e.g. as described by Sangmam, et. al. (*Synth.Commun.*, 1998, 28, 2945-58) for retinoic acid amides.

Compounds of general formula (I) wherein R" represents $CH_2OH$ can be prepared starting from compounds of general Formula (I) wherein R" represents COOH or from their esters or derivatives through procedures known in literature for the synthesis of alcohols, for example, for reduction with $LiAlH_4$.

EXAMPLE 1

Preparation of 4-(3-(1-Adamantyl)-4-tert-butyldimethylsilyloxyphenyl)benzaldehyde The title compound was prepared following synthesis diagram 1 reported as follows.

Synthesis diagram 1

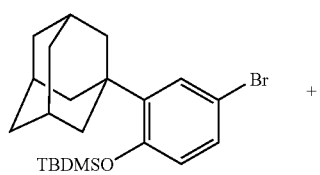

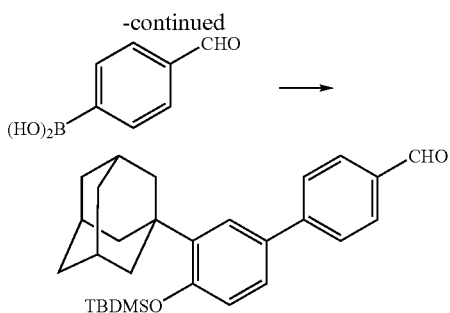

1.56 g (3.70 mmol) of 4-tert-butyldimethylsilyloxy-3-(1-adamantyl)-bromobenzene [Charpentier et al. *J. Med. Chem.*, 1995, 38, 4993-5006], were dissolved in 7.5 ml of toluene. 3.7 ml of a 2M aqueous solution of $Na_2CO_3$, 0.128 g (0.11 mmol) of tetrakistriphenylphosphine-palladium, and a solution of 610 mg (4.07 mmol) of 4-formylbenzeneboronic acid in 1.73 ml of ethanol were added. The solution thus obtained was he refluxed for 2 hours in a current of nitrogen. The solution was then cooled, taken up with ethyl acetate, and washed with a NaCl saturated solution.

The phases were separated, the organic phase was filtered, dried over $Na_2SO_4$, filtered again, the solvent was evaporated and the residue subjected to flash chromatography on silica gel (Merck), using hexane:ethyl acetate 3:1 as eluent.

1.09 g of the title compound was obtained.

M.p. 158° C.

$^1$HNMR ($CDCl_3$) δ:0.37 (6H, s, —Si($CH_3$)$_2$); 1.05 (9H, s, -t-Bu); 1.78 (6H, s, 6Ad.); 2.09 (3H, s, 3Ad.); 2.15 (6H, s, 6Ad.); 6.88 (1H, d, 1Ar, J=8.54 Hz); 7.35 (1H, dd, 1Ar, J2.24 Hz, J=8.54 Hz); 7.51 (1H, d, 1Ar, J=2.24 Hz); 7.70 (2H, d, 2Ar, J=8.14 Hz); 7.90 (2H, d, 2Ar, J=8.14 Hz); 10.01 (1H, s, —CHO).

EXAMPLE 2

Preparation of methyl E-4(3-(1-Adamantyl)-4-tert-butyldimethylsilyloxyphenyl)cinnamate The title compound was prepared according to the following synthesis scheme 2.

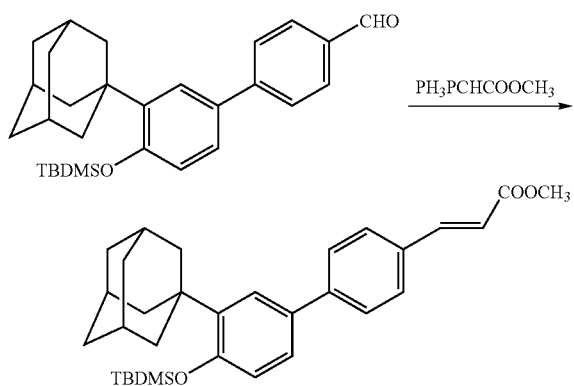

386 mg (0.864 mmol) of 4-(1-tert-butyldimethylsilyloxy-2-(1-adamantyl)phenyl))-benzaldehyde were dissolved in 4.5 ml of chloroform, 298 mg (0.864 mmol) of methyl triphenylphosphoranylidenacetate were added and the solution thus obtained was refluxed for three hours. The solution was cooled, the solvent evaporated, and then subjected to flash Chromatography on silica gel (Merck), using hexane:$CH_2Cl_2$ 1:1 as eluent. 350 mg of the title compound were obtained.

M.p. 148° C.

$^1$HNMR ($CDCl_3$) δ:0.36 (6H, s, —Si($CH_3$)$_2$); 1.05 (9H, s, -t-Bu); 1.77 (6H, s, 6Ad.); 2.08 (3H, s, 3Ad.); 2.15 (6H, s, 6Ad.); 3.80 (3H, s, —$OCH_3$); 6.44 (1H, d, —CH=, J=16.07 Hz); 6.86 (1H, d, 1Ar, J=8.54 Hz); 7.30 (1H, dd, 1Ar, J=2.24 Hz, J=8.54 Hz); 7.47 (1H, d, 1Ar, J=2.24 Hz); 7.50-7.70 (4H, m, 4Ar); 7.71 (1H, d, CH=, J=16.07 Hz).

EXAMPLE 3

Preparation of methyl E-4-(3-(1-adamantyl)-4-hydroxyphenyl)cinnamate

The title compound was prepared according to the following synthesis scheme 3.

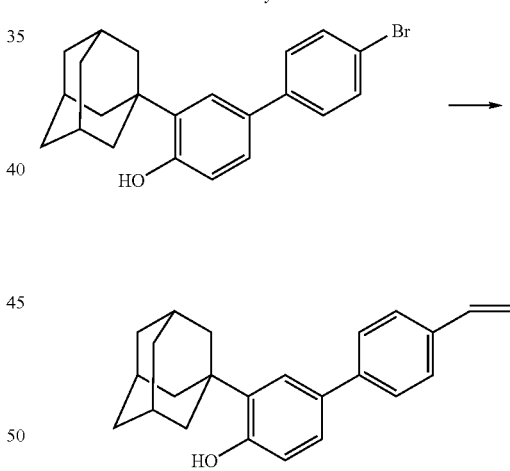

A mixture of 1 g (2.6 mmol) of 2-(1-adamantyl)-4-(4-bromophenyl)phenol, 358 mg (4.16 mmol) of methyl acrylate, 5.8 mg (0.02 mmol) of Palladium acetate and 30 mg (0.1 mmol) of tri-(o-tolyl)-phosphine in 1.2 ml of triethylamine was refluxed for 4 hours. The triethylamine was evaporated, taken up with 2N HCl and ethyl acetate, the organic phases were separated, washed with water, dried over $Na_2SO_4$, and the solvent evaporated. 640 mg of product were obtained.

M.p.>240° C.

$^1$H-NMR (DMSO-d6) δ:1.75 (6H), 2.1 (9H), 3.72 (s, 3H, OCH3), 6.63 (d, 1H, J=16 Hz), 6.85 (dd, 1H, J=8.8, 1.8 Hz), 7.3-7.4 (2H arom.), 7.55-7.85 (5H), 9.55 (s, 1H, OH).

EXAMPLE 4

Preparation of E-4-(3-(1-adamantyl)-4-hydroxyphenyl)cinnamic acid (ST 1926)

The title compound was prepared according to the following synthesis scheme 4.

Synthesis scheme 4

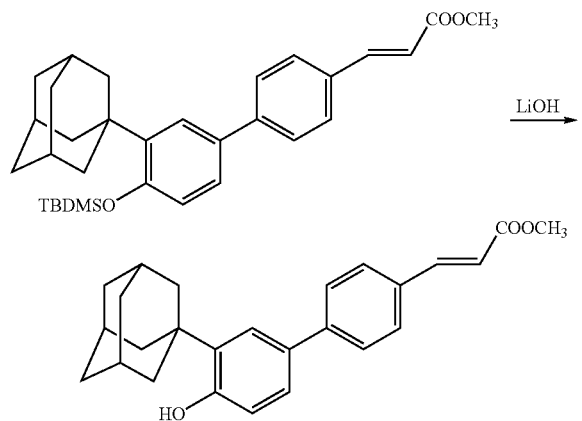

42 mg (1 mmol) of LiOH.H₂O were dissolved in 8.2 ml of THF (tetrahydrofuran):H₂O 1:1, 100 mg (0.2 mmol) of methyl E-4(3-(1-adamantyl)-4-tert-butyldimethylsilyloxyphenyl)cinnamate were added and the solution thus obtained was kept under stirring at room temperature for 3 hours. The THF was evaporated, acidified with 2N HCl, extracted with ethyl acetate and dried over Na2SO₄. Filtered and evaporated, it was then subjected to flash chromatography on silica gel (Merck) with hexane:ethyl acetate 2:3, then 1:1, as eluent. 55 mg of product were obtained.

M.p.>240° C. $R_f$=0.50 (Merck silica gel 60F$_{254}$, EtOAc)

¹HNMR (DMSO-d₆) δ:1.74 (6H, s, 6Ad.); 2.04 (3H, s, 3Ad.); 2.12 (6H, s, 6Ad.); 6.51 (1H, d, —CH═, J=16.18 Hz); 6.85 (1H, d, 1Ar, J=8.82 Hz); 7.30-7.40 (2H, m, 2Ar); 7.55-7.63 (3H, m, 2Ar+CH═); 7.70 (2H, d, 2Ar, J=8.09 Hz); 9.54 (1H, s, —OH); 12.34. (1H, brs, —COOH).

MS (m/z):374 (M⁺, 100).

EXAMPLE 5

Preparation of methyl 4-(3-(1-adamantyl)-4-methoxyphenyl)propiolate

The title compound was prepared according to the following synthesis scheme 5.

Synthesis scheme 5

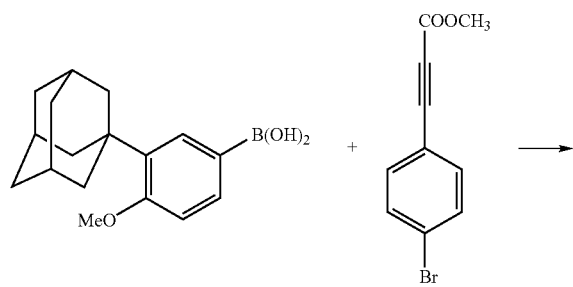

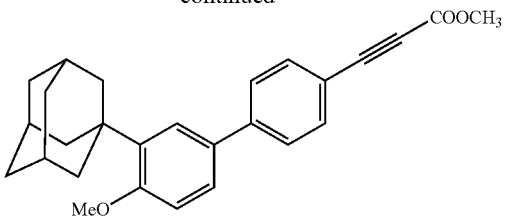

301 mg (1.26 mmol) of methyl 4-bromophenylpropiolate were dissolved in 2.5 ml of toluene, 1.34 ml of an aqueous solution of 2M Na₂CO₃, then 43.7 mg of Pd-tetrakistriphenylphosphine, and finally 398 mg (1.39 mmol) of 3-(1-adamantyl)-4-methoxyphenylboronic acid were added, and the mixture refluxed for 3 hours. The crude product was taken up in ethyl ether, the organic phase washed with a saturated NaCl solution, dried over Na₂SO₄, evaporated to dryness to give 570 mg of crude product. Flash chromatography on silica gel (Merck) with hexane:ethyl acetate 2:1 as eluent gave 15 mg of pure product.

M.p. 175° C.

¹H-NMR (CDCl₃) δ:3.86 (s, 3H, OCH₃), 3.90 (s, 3H, OCH₃), 6.96 (d, 1H, J=8.5), 7.43 (dd, 1H, J=2.2, 8.5), 7.47 (d, 1H, J=2.2), 7.55.7.70 (4H arom.).

EXAMPLE 6

Preparation of 4-(3-(1-adamantyl)-4-methoxyphenyl)propiolic acid (ST 1879)

The title compound was prepared according to the following synthesis scheme 6.

Synthesis scheme 6

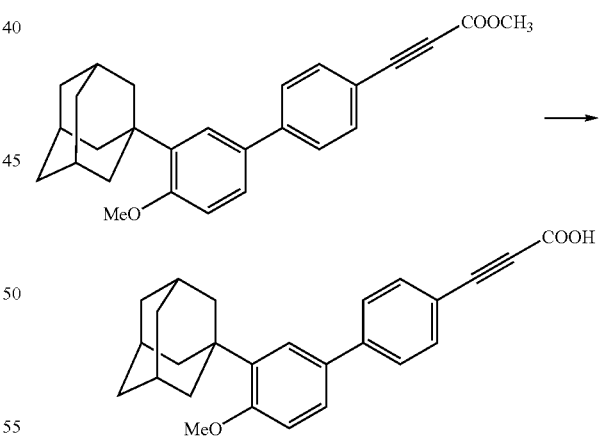

15 mg (0.0374 mmol) of methyl E-4-(3-(1-adamantyl)-4-methoxyphenyl)propiolate were dissolved in 2.14 ml of 0.7N NaOH in methanol, and the mixture refluxed for 1 hour. The methanol was evaporated, taken up in water, and acidified with 6N HCl, and extracted with ethyl ether. After drying over Na₂SO₄ and having evaporated the solvent, the residue was washed with hexane, from which were obtained after filtration 10 mg of product.

M.p. 156° C. $R_f$=0.41 (Merck silica gel 60F$_{254}$, EtOAc/MeOH 2/1)

$^1$H-NMR (DMSO-d$_6$) δ:1.70 (s, 6H), 2.10 (s, 9H), 3.85 (s, 3H, OCH$_3$), 7.05 (d, 1H, J=8.4, H-6'), 7.40 (d, 1H, J=2, H-2'), 7.45-7.60 (3H arom.), 7.65 (2H arom.)

EXAMPLE 7

Preparation of E-4-(3-(1-adamantyl)-4-methoxyphenyl)cinnamyl alcohol

The title compound was prepared according to the following synthesis scheme 7.

Synthesis scheme 7

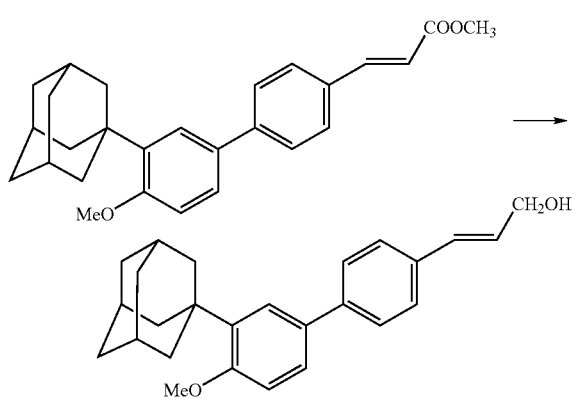

375 µl of a 1M solution of LiAlH$_4$ in tetrahydrofuran (0.365 mmol) were added to 5 ml of anhydrous tetrahydrofuran. Cooling in an ice bath, 151 mg (0.375 mmol) of methyl E-4-(3-(1-adamantyl)-4-methoxyphenyl)cinnamate (see Example 19) were added, stirred for 1 hour in the cold, then overnight at room temperature. Chilled in an ice bath, 5 ml of an aqueous solution of 10% NH$_4$Cl were added, the tetrahydrofuran was evaporated and then taken up with ethyl acetate. The organic phase was separated and dried over Na$_2$SO$_4$. By evaporating the solvent 126 mg of crude product were obtained, which were chromatographed on silica gel (Merck) with methylene chloride: hexane 3:1, then again with hexane: ethyl acetate 28:72 as eluent, to give 11 mg of product.

M.p. 148° C.

$^1$H-NMR (CDCl$_3$) δ:1.75 (s, 6H), 2.15 (9H), 3.90, s, 3H, OCH$_3$), 4.38 (dd, 2H, J=6, 1.6), 6.41 (dt, 1H, J=6, 16, =CHCH$_2$OH), 6.67 (dd, 1H, J=1.6, 16, ArylCH=), 6.96 (d, 1H, J=8.3, H-6'), 7.42 (dd, 1H, J=2.2, 8.3, H-5'), 7.45 (m, 2H, H-2 e H-6), 7.48 (d, 1H, J=2.2, H-3'), 7.55 (m, 2H, H-3 e H-5)

MS m/z 374 (M$^+$).

EXAMPLE 8

Preparation of methyl E-4-(4-hydroxyphenyl)cinnamate

The title compound was prepared according to the following synthesis scheme 8.

Synthesis scheme 8

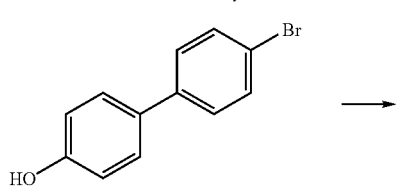

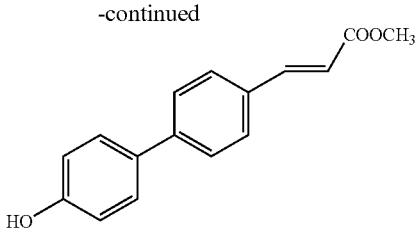

A mixture of 2 g (8.03 mmol) of 4-(4-bromophenyl)phenol, 1.1 g (12.8 mmol) of methyl acrylate, 18 mg (0.08 mmol) of Palladium acetate, and 94 mg (0.31 mmol) of tri-(o-tolyl) phosphine in 3.7 ml of triethylamine was refluxed for 6 hours. A further 6 mg of Palladium acetate and 30 mg of tri-(o-tolyl) phosphine were added and heated for an hour, then a further 30 mg of Palladium acetate and 94 mg di tri-(o-toluyl)phosphine were added and heated for 3.5 hours. Then the reaction was acidified with 6M HCl, ethyl acetate was added, and stirred for a time to dissolve the precipitate, the phases were separated, the organic phase dried over Na$_2$SO$_4$ and the solvent evaporated. The crude product (934 mg) was purified by taking up in hexane/ethyl ether and filtered off to give 1.7 g of the title product.

M.p. 233-235° C.

$^1$NMR (CDCl$_3$) δ:3.70 (s, 3H, OCH$_3$), 6.13 (d, 1H, CH=, J=16), 6.82 (d, 2H, H-3' e H-5), 7.48, d, 2H, H-2' e H-6), 7.6-7.75 (5H).

EXAMPLE 9

Preparation of methyl E-4-(3-(1-methylcyclohexyl)-4-hydroxyphenyl)cinnamate

The title compound was prepared according to the following synthesis scheme 9.

Synthesis scheme 9

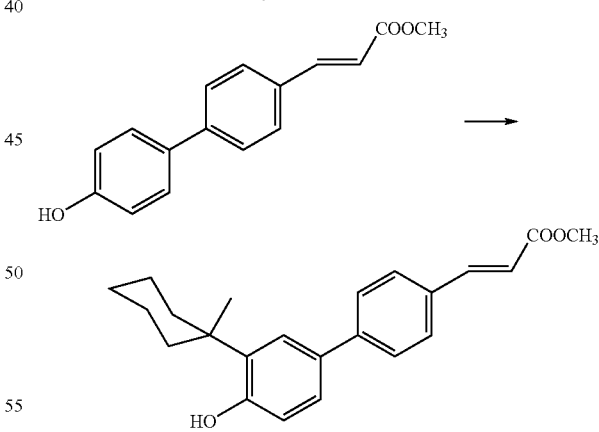

150 mg (0.6 mmol) of methyl E-4-(4-hydroxyphenyl)cinnamate and 68.5 mg of 1-methyl-1-cyclohexanol were dissolved in 1.2 ml of CH$_2$Cl$_2$, treated with 0.032 ml of concentrated H$_2$SO$_4$ and the mixture refluxed for one day. Water was added and the mixture neutralised with a saturated sodium bicarbonate solution. The aqueous phase was extracted several times with ethyl acetate, dried over Na$_2$SO$_4$, filtered and evaporated. The resulting crude was flash chromatographed on silica gel (Merck), with hexane:ethyl acetate 9:1 as eluent. 20 mg of product were obtained.

$^1$HNMR (acetone-d6) δ:1.43 (3H, s, —CH3); 1.4-1.9 (8H, m, cyclohex.); 2.3-2.45 (2H, m, cyclohex.); 3.80 (3H, s, —OCH3); 6.60 (1H, d, CH═, J=16.18 Hz); 7.0 (1H, d, 1Ar, J=8.2 Hz); 7.44 (1H, dd, 1Ar, J=8.2 Hz, 2.2 Hz); 7.65 (1H, d, 1Ar, J=2.2 Hz); 7.7-7.85 (5H, m, 4Ar+CH═); 8.65 (1H, s, —OH).

EXAMPLE 10

Preparation of 2-(1-adamantyl)-4-bromo-6-N-phthalimidomethyl)phenol

The title compound was prepared according to the following synthesis scheme 10.

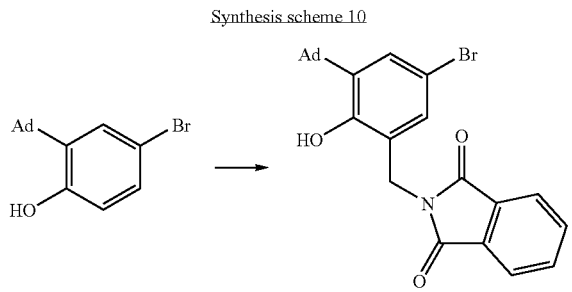

To a solution of 500 mg (1.63 mmol) of 2-adamantyl-4-bromophenol in 7 ml of dichloromethane were added 289 mg (1.63 mmol) of N-hydroxymethylphthalimide and two drops of concentrated H$_2$SO$_4$. The mixture was refluxed for three hours, diluted with water, and extracted with dichloromethane. Evaporation of the solvent and chromatography on silica gel with hexane:ethyl acetate 80:20 as eluent gave 348 mg (46%) of product.

M.p. 253° C.

$^1$H NMR (CDCl$_3$) δ:1.78 (6H, s, 6Ad.); 2.09 (3H, s, 3Ad.9; 2.12 (6H, s, 6Ad.); 4.76 (2H, s, —CH$_2$—); 7.28 (1H, d, 1Ar, J=2.94 Hz), 7.45 (1H, d, 1Ar, J=2.94 Hz); 7.76 (2H, dd, 2Ar, J=2.94 Hz, J=5.52 Hz); 7.88 (2h, dd, 2Ar, J=2.94 Hz, J=5.52 Hz); 8.13 (1H,s, —OH).

EXAMPLE 11

Preparation of methyl E-4-(3-(1-adamantyl)-5-(N-phthalimidomethyl)-4-hydroxyphenyl)cinnamate The title compound was prepared according to the following synthesis scheme 11.

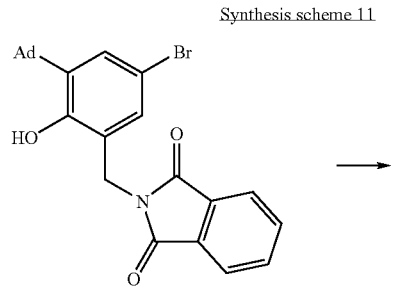

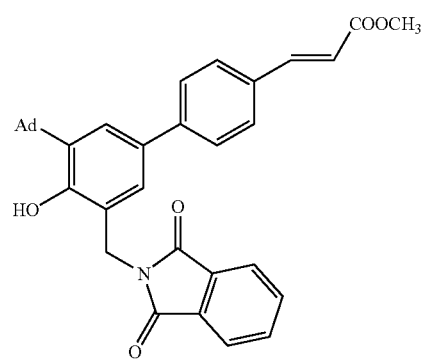

100 mg of 2-(1-adamantyl)-4-bromo-6-N-phthalimidomethyl)phenol were suspended in 1.6 ml of dioxane and under nitrogen flow; 59.7 mg of boro(bispinacolate), 63 mg of anhydrous potassium acetate, 5 mg of Dichloro(diphenylphosphineferrocene)palladium and 103 mg of methyl 4-bromocinnamate were added. This was refluxed for 2 hours, resuspended in ethyl acetate, acidified with 1 ml of 2M HCl, the organic phase washed with a saturated NaCl solution, dried over Na$_2$SO$_4$, the solvent evaporated and chromatographed on silica gel with hexane:ethyl acetate 65:35. 32 mg (27%) of product were obtained.

M.p. 216° C.

$^1$HNMR (CDCl$_3$) δ:1.78 (6H, s, 6Ad.); 2.09 (3H, s, 3Ad.); 2.12 (6H, s, 6Ad.); 3.83 (3H, s, —OCH3); 4.90 (2H, S, —CH$_2$—); 6.44 (1H, d, CH═, J=16.18 Hz); 7.45-7.90 (11H, m, 10 Ar+CH═); 8.22 (1H,s, —OH).

MS (m/z):547 (M$^+$, 100); 400 (30); 160 (30).

EXAMPLE 12

Preparation of E-4-(3-(1-adamantyl)-5-(N-phthalimidomethyl)-4-hydroxyphenyl)cinnamic acid The title compound was prepared according to the following synthesis scheme 12.

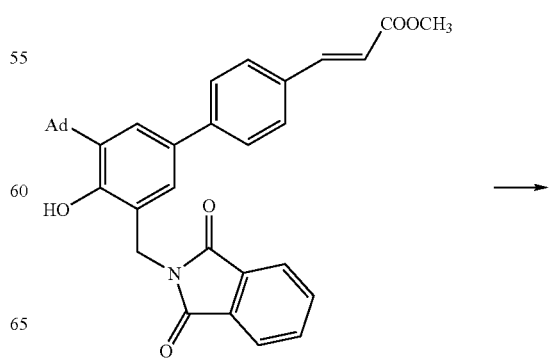

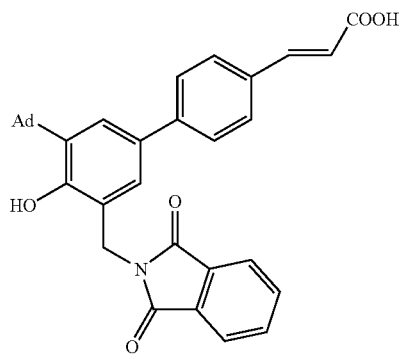

30 mg of methyl E-4-(3-(1-adamantyl)-5-(N-phthalimidomethyl)-4-hydroxyphenyl)cinnamate were added to 1 ml of a 3:1 mixture of acetic acid and 37% hydrochloric acid and the mixture refluxed for 30 hours. The acetic acid was evaporated, and then taken up with water, the solid residue filtered and washed with water. 24 mg of product was obtained.

M.p. 216° C.

$^1$HNMR (DMSO-d$_6$) δ:1.73 (6H, s, 6Ad.); 2.04 (3H, s, 3Ad.); 2.12 (6H, s, 6Ad.); 4.81 (2H, s, —CH$_2$—); 6.45 (1H, d, —CH═, J=16.18 Hz); 7.07 (1H, d, 1Ar, J=1.84 Hz); 7.30 (1H, d, 1Ar, J=1.84 Hz); 7.46 (2H, dd, 2Ar, J=8.82 Hz, J=1.84 Hz); 7.53 (1H, d, —CH═, J=16.18 Hz); 7.64 (2H, dd, 2Ar, J=8.82 Hz, J=1.84 Hz); 7.78-7.94 (4H, m, 4Ar); 8.60 (1H, s, —OH); 12.5 (1H, brs, COOH).

MS (m/z):533 (M$^+$, 100); 386 (40); 160 (60) 130 (50).

EXAMPLE 13

Preparation of E-4-(3-(1-adamantyl)-5-(aminomethyl)-4-hydroxyphenyl)cinnamic acid The title compound was prepared according to the following synthesis scheme 13.

Synthesis scheme 13

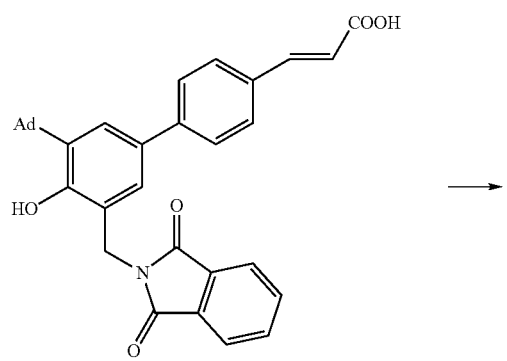

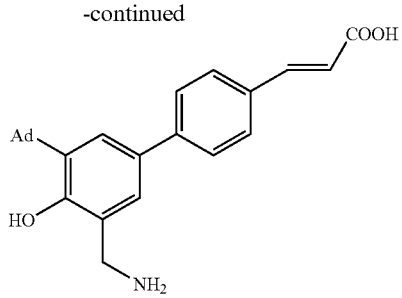

20 mg of E-4-(3-(1-adamantyl)-5-(N-phthalimidomethyl)-4-hydroxyphenyl)cinnamic acid were suspended in 0.15 ml of methanol, 0.013 ml of hydrazine hydrate were added and the mixture heated for 5 hours at 50° C. The solvent was evaporated, resuspended in water, acidified with 2M HCl and the precipitate filtered under vacuum. The crude product was dried, treated with tetrahydrofuran to dissolve the phthalylhydrazide, and filtered.

M.p. 195° C.

$^1$HNMR (DMSO-d$_6$) δ:1.73 (6H, s, 6Ad.); 2.04 (3H, s, 3Ad.); 2.12 (6H, s, 6Ad.); 4.00 (2H, s, —CH$_2$—); 6.45 (1H, d, —CH═, J=16.18 Hz); 7.07-8.00 (5H, m, 5Ar).

EXAMPLE 14

Preparation of 4-(7-Adamantan-1-yl-benzo(1,3)dioxol-5-yl)-benzaldehyde

The title compound was prepared according to the following synthesis scheme 14.

Synthesis scheme 14

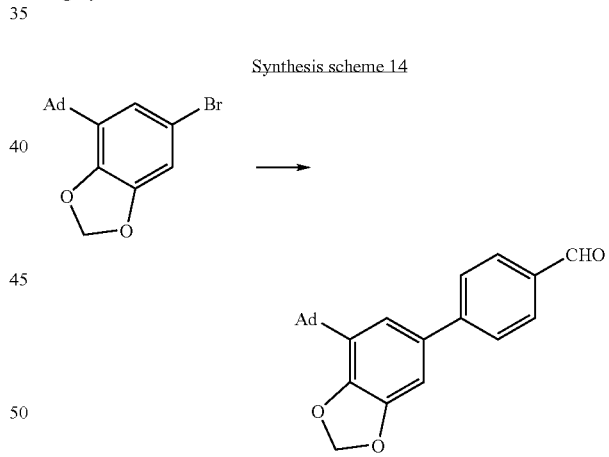

0.875 g (2.61 mmol) 4-Adamantan-1-yl-6-bromo-benzo(1,3)dioxol were dissolved in 5.2 ml of toluene and 2.6 ml of a 2M aqueous solution of Na$_2$CO$_3$, 0.090 g (0.08 mmol) of tetrakis-triphenylphosphine-palladium, and a solution of 0.430 g (2.87 mmol) of 4-formylbenzeneboronic acid in 1.2 ml of ethanol were added. This was refluxed for 7 hours under nitrogen current. This was cooled, taken up in ethyl acetate and washed with a saturated NaCl solution. The organic phase was dried over Na$_2$SO$_4$, filtered and the solvent evaporated. After flash chromatography on silica gel (Merck), with hexane:ethyl acetate 9:1 as eluent, 0.66 g of product (70%) are obtained.

$^1$H NMR (CDCl$_3$) δ:1.80 (6H, s, 6Ad.); 2.09 (3H, s, 3Ad.); 2.12 (6H, s, 6Ad.); 6.02 (2H, s, —CH$_2$—); 7.01 (1H, d, 1Ar,

J=1.86 Hz); 7.04 (1H, d, 1Ar, J=1.86 Hz); 7.68 (2H, d, 2Ar, J=8.19 Hz,); 7.92 (2H, d, 2Ar, J=8.19 Hz,); 10.02 (1H, s, —CHO).

EXAMPLE 15

Preparation of methyl E-4-(7-Adamantan-1-yl-benzo (1,3)dioxol-5-yl)-cinnamate

The title compound was prepared according to the following synthesis scheme 15.

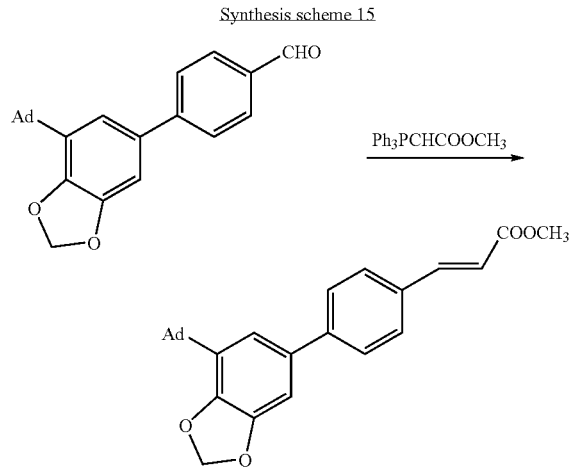

A solution of 300 mg of 4-(7-adamantan-1-yl-benzo(1,3) dioxil-5-yl)-benzaldehyde in 4.5 ml of CHCl$_3$ was treated under nitrogen with 278 mg of methyl triphenylphosphoranylidenacetate and refluxed for 5 hours, with a further addition of ylide (20%) after 3 hours. At the end of this period the solvent was evaporated, and the residue chromatographed on silica gel with hexane:dichloromethane 45:55 as eluent. 298 mg of product were obtained.

M.p. 205° C.

$^1$H NMR (CDCl$_3$) δ:1.72 (6H, s, 6Ad.); 2.06 (3H, s, 3Ad.); 2.12 (6H, s, 6Ad.); 3.80 (3H, s, —OCH$_3$); 5.97 (2H, s, —CH$_2$—); 6.44 (1H, d, —CH═, J=16 Hz); 6.95 (1H, d, 1Ar, J=1.86 Hz); 6.98 (1H, d, 1Ar, J=1.86 Hz); 7.52-7.58 (4H, m, 4Ar); 7.71 (1H, d, —CH═, J=16 Hz,).

EXAMPLE 16

Preparation of E-4-(7-adamantan-1-yl-benzo(1,3) dioxol-5-yl)-cinnamic acid

The title compound was prepared according to the following synthesis scheme 16.

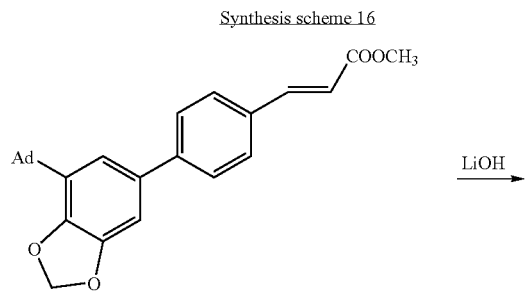

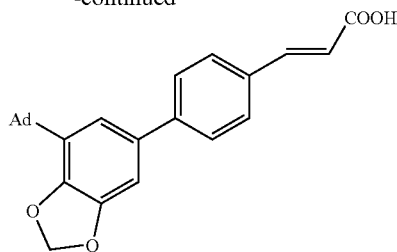

200 mg (0.48) methyl E-4-(7-adamantan-1-yl-benzo(1,3) dioxol-5-yl)-cinnamate were suspended in a solution of LIOH.H$_2$O in 25 ml of THF/H$_2$O 3:2 and kept under stirring overnight at room temperature. The THF was evaporated, the carboxylate suspension washed with hexane, then acidified with 2N HCl and chilled in an ice bath. After filtration 150 mg (78%) of product were obtained.

M.P.>300° C. R$_f$=0.59(Merck silica gel 60F$_{254}$, EtOAc/Hexane 9/1)

$^1$H NMR (DMSO-d$_6$) δ 1.72 (6H, s, 6Ad.); 2.01 (3H, s, 3Ad.); 2.12 (6H, s, 6Ad.); 6.01 (2H, s, —CH$_2$—); 6.52 (1H, d, —CH═, J=16.18 Hz); 6.99 (1H, d, 1Ar, J=1.84 Hz); 7.14 (1H, d, 1Ar, J=1.84 Hz); 7.60 (1H, d, —CH═, J=16.18 Hz); 7.62 (2H, dd, 2Ar, J=8.46 Hz, 1.84Hz); 7.68 (2H, dd, 2Ar, J=8.46 Hz, 1.84 Hz).

EXAMPLE 17

Preparation of methyl 2-[4-(3-(1-adamantyl)-4-hydroxyphenyl)]cyclopropanecarboxylate The title compound was prepared according to the following synthesis scheme 17.

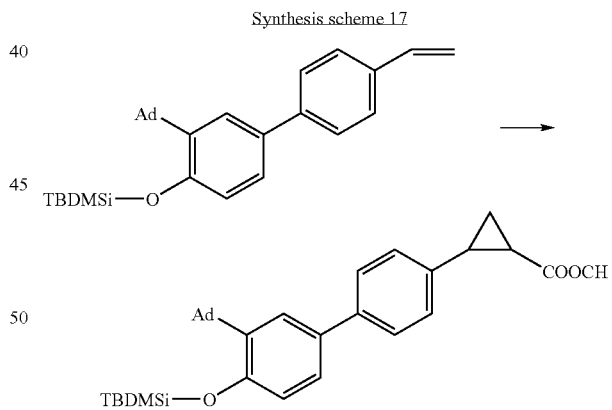

0.5 mg of rhodium tetraacetate bihydrate and 36 μl of ethyl diazoacetate were added to a solution of 150 mg of (3-adamantan-1-yl-4'-vinylbiphenyl-4-oxy)tert-butyldimethylsilane, prepared from the corresponding aldehyde through Wittig reaction, in 2 ml of dichloromethane. The reaction was left for 5 days at room temperature, with the addition of a total of 5 mg of catalyst and 10 pi of ethyl diazoacetate. The catalyst was filtered through celite, dried over sodium sulphate, evaporated, chromatographed on silica gel with a 65:35 mixture of hexane:ethyl acetate.

43 mg of a mixture of the two diastereoisomers cis and trans were obtained.

¹H NMR (CDCl₃) δ; 0.45 (6H, s, —Si(CH₃); 0.95 (3H, t, —CH₃, J=7 Hz); 1.1 (9H, s, tBu); 1.25 (3H, t, —CH₃, J=7 Hz ); 1.35-1.55 (1H, m, 1-CH₂); 1.55-1.74 (1H, m, 1-CH₂); 1.79 (6H, s, 6Ad.); 1.95 (1H, m, —CH—COOEt) 2.07 (3H, s, 3Ad.); 2.12 (6H, s, 6Ad.); 2.48-2.65 (1H, m, —CH—Ar); 3.85 (2H, q, —OCH₂, J=7 Hz); 4.18 (2H, q, —OCH₂, J=7 Hz); 6.82 (1H, dd, 1Ar, J=1.84 Hz, 8.46 Hz); 7.15 (1H, d, 1Ar, J=8.46 Hz); 7.25 (2H, dd, 2Ar, J=8.0 Hz, 1.84 Hz); 7.45-7.50 (3H, m, 3Ar).

EXAMPLE 18

Preparation of the cis and trans 2-(4-(3-(1-adamantyl)-4-hydroxyphenyl)]cyclopropanecarboxylic acids The title compounds were prepared according to the following synthesis scheme 18.

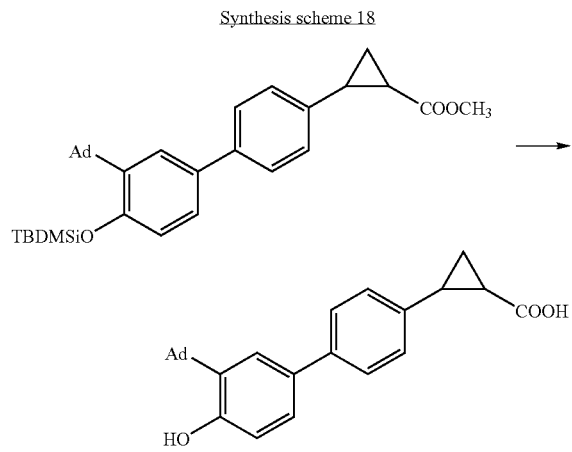

113 mg of KF on finely crushed Al₂O₃ (40%) were added to a solution of methyl 2-[4-(3-(1-adamantyl)-4-hydroxyphenyl)]cyclopropanecarboxylate (110 mg) in 4.4 ml of dimethoxyethane, and stirred at room temperature for 2 days. After filtration, the solvent was evaporated, the crude product was added to a solution of 63 mg of LiOH.H₂O in 12.4 ml of 50% tetrahydrofuran in water. This was stirred at room temperature for three days, the solvent evaporated, extracted with ethyl ether, acidified with 2M HCl, and extracted with ethyl acetate. After evaporation, the product (58 mg) was chromatographed on silica gel with hexane:ethyl acetate 40:60. 6 mg of trans-2-4-(3-(1-adamantyl)-4-hydroxyphenyl)]cyclopropanecarboxylic acid M.p. 190° C., 10 mg of a mixture of diastereoisomers and 20 mg of cis-2-[4-(3-(1-adamantyl)-4-hydroxyphenyl)]cyclopropanecarboxylic acid were obtained.

M.p, 204° C.

R$_f$=0.23 cis; 0.44 trans (Merck silica gel 60F₂₅₄, EtOAc/Hexane 6/4)

¹H NMR (MeOD) δ Trans:1.45-1.50 (1H, m, 1-CH₂); 1.60-1.65 (1H, m, 1-CH₂); 1.95-2.0 (7H, m, —CH—COOEt+6Ad) 2.2 (3H, s, 3Ad.); 2.35 (6H, s, 6Ad.); 2.50-2.58 (1H, m, —CH—Ar); 6.84 (1H, d, 1Ar, J=8.46 Hz); 7.24 (2H, dd, 2Ar, J=7.35 Hz, J=1.84 Hz); 7.31 (1H, dd, 1Ar, J=8.46 Hz, 2.57 Hz); 7.42 (1H, d, 1Ar, J=2.57 Hz); 7.52 (2H, dd, 2Ar, J=7.35 Hz, J=1.84 Hz).

¹H NMR (MeOD) δ Cis:1.40-1.50 (1H, m, 1-CH₂); 1.70-1.75 (1H, m, 1-CH₂); 1.95-2.0 (6H, s, 6Ad); 2.10-2.15 (4H, m, 3Ad+—CH—COOH); 2.30 (6H, s, 6Ad.); 2.70-2.78 (1H, m, —CH—Ar); 6.83 (1H, d, 1Ar, J=8.46 Hz); 7.30 (1H, dd, 1Ar, J=8.46 Hz, 2.57 Hz); 7.38 (2H, dd, 2Ar, J=7.30 Hz, J=1.84 Hz); 7.42 (1H, d, 1Ar, J=2.57 Hz); 7.49 (2H, dd, 2Ar, J=7.30 Hz, J=1.84 Hz).

MS (m/z):388 (M⁺, 100); 135 (50).

EXAMPLE 19

Preparation of methyl E-4-(3-(1-adamantyl)-4-methoxyphenyl)cinnamate

The title compound was prepared according to the following synthesis scheme 19.

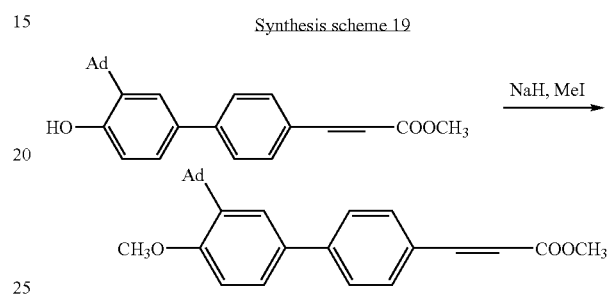

To a suspension of NaH (60% in mineral oil, 66 mg, 2.74 mmol) in 3.3 mL of DMF, under N₂, 969 mg (2.49 mmol) of methyl E-4(3-(1-adamantyl)-4-hydroxycinnamate were added. The mixture was stirred at room temperature for 1 h, then 186 μL (2.99 mmol) of CH₃I were dropped.

The reaction was left overnight at room temperature; after addition of 80 ml of cold water the aqueous phase was extracted with CH₂Cl₂ (4×60 ml). The organic layers were washed with water, dried over Na₂SO₄ and the solvent evaporated. 972 mg of product were obtained (97%).

¹H-NMR (CDCl₃) δ:1.75 (6H), 2.1 (9H), 3.75 (s, 3H, OCH3), 3.80 (s, 3H, —COOCH₃); 6.40 (d, 1H, CH=, J=16 Hz), 6.90 (d, 1H, 1 Ar, J=8.8 Hz), 7.35 (dd, 1H, 1Ar, J=8.8, 1.8.Hz); 7.42 (d, 1H, 1 Ar, J=1.8 Hz); 7-48-7.53 (m, 4H, 4 Ar); 7.65 (d, 1H, CH=, J=16 Hz).

EXAMPLE 20

Preparation of E-4-(3-(1-adamantyl)-4-methoxyphenyl)cinnamic acid (ST 1898)

The title compound was prepared according to the following synthesis scheme 20

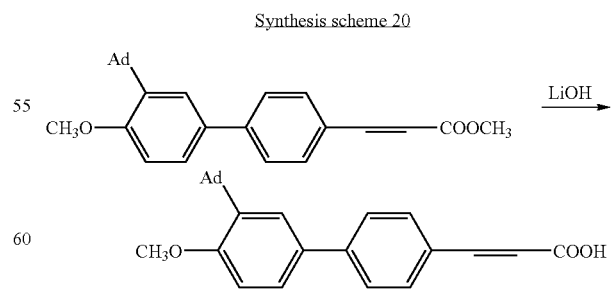

455 mg (10.8 mmol) of LiOH.H₂O were dissolved in 90 ml of THF:H₂O 1:1; 873 mg (2.17 mmol) of methyl E-4(3-(1-adamantyl)-4-methoxyphenyl)cinnamate were added and the solution thus obtained was kept under stirring at room temperature for 2 days. The THF was evaporated, acidified with 2N HCl and the white precipitate was filtered. The solid was washed with AcOEt and Et$_2$O, to obtain 792 mg (94%) of the title compound.

$R_f$=0.28 (Merck silica gel 60F$_{254}$, EtOAc/Hexane 9/1)
$^1$HNMR (DMSO-d$_6$) δ:1.74 (6H, s, 6Ad.); 2.04 (3H, s, 3Ad.); 2.12 (6H, s, 6Ad.); 3.75 (3H, s, —OCH$_3$); 6.50 (1H, d, —CH═, J=16 Hz); 6.98 (1H, d, 1Ar, J=8.8 Hz); 7.40-7.70 (7H, m, 6Ar+CH═); 12.3 (1H, brs, —COOH).

Cytotoxicity of ST1926 Towards Tumoral Cell Lines

To carry out the cytotoxicity tests, two acute promyelocytic leukaemia (APL) cell lines were used.
1. Cell line NB4, carrying the chromosomal translocation t(15;17) which generates the fusion protein PML/RARα. This cell line is extremely sensitive to the differentiating action of pharmaceutical doses of ATRA ($10^{-7}$-$10^{-6}$ M);
2. Cell line HL60, which responds to ATRA less sensitively with respect to cell line NB4. This cell line does not carry the chromosomal translocation mentioned above.

These cell lines were maintained in RPMI 1640 containing 10% foetal calf serum (FCS) and 1% glutamine.

Different cell lines deriving from solid tumors were also used.
1. Human prostate carcinoma PC3 and DU145. These cell lines were maintained in RPMI 1640 medium containing 10% FCS, 1% sodium pyruvate and 1% glutamine;
2. Human colon adenocarcinoma LoVo. This cell line was maintained in HAM's F-12 medium, containing 10% FCS and 1% glutamine.
3. Human ovarian carcinoma such as A2780 and A2780/Dx, sensitive and resistant to drugs, respectively (doxorubicin, taxol, etoposide, vincristine); IGROV-1 and IGROV-1/Pt, sensitive and resistant to platinum-based chemotherapy, respectively, were maintained in RPMI 1640 medium containing 10% FCS, 1% sodium pyruvate and 1% glutamine;
4. Human melanoma MeWo and MeS 2.21, glioblastoma GBM, no small cell lung carcinomas A-431, NCI-H460, osteosarcomas SAOS and U20S were maintained in RPMI 1640 medium containing 10% FCS, 1% sodium pyruvate and 1% glutamine.

The cytotoxicity tests were carried out using NB4 or HL-60 cells in suspension (10000/well). The cells were seeded in a volume of 250 μl in 96 well plates and incubated for 24 hours at 37° C. The following day, test compound ST 1926 [(2E)-3-[3'-(1-Adamantyl)-4'-hydroxy[1,1'-biphenyl]-4-yl]-2-propenoc/ic acid] was added at increasing concentrations, and the cells were incubated for a further 24 hours at 37° C. in a humidified atmosphere containing 5% CO$_2$. On the 3$^{rd}$ day, the medium was removed by centrifuging the plate at 1600×g for 10 min and the supernatant decanted. 250 μl of PBS were added; then the plates were centrifuged again at 1600×g for 10 minutes and the supernatant decanted. 200 μl/well of RPMI 1640 medium containing 10% FCS were added and the plates were incubated at 37° C. for a further 48 hours. On the 5$^{th}$ day, the plates were again centrifuged at 1600×g for 10 minutes, and the medium was removed by upturning the plates, 200 μl of PBS and 50 μl of cold, 80% TCA were added. The plates were then left to incubate on ice for at least 1 hour. The TCA was removed by upturning; the plates were washed three times by immersion in distilled water and dried first on paper, then with a jet of hot air. To all wells were added 200 μl of 0.4% sulphorodamine B in 1% acetic acid. The plates were incubated at room temperature.for a further 30 minutes. The sulphorodamine B was removed by upturning, the plates were washed by immersion in 1% acetic acid three times, then dried firstly with absorbent paper, then with a jet of hot air. 200 μl of 10 mM Tris base were added into all the wells and the plates were stirred for at least 20 min. The optical density was measured using a Multiskan spectrophotometer at 540 nm.

For the adherent cells, the procedure adopted was the same, whilst the washing of the plates on the 3$^{rd}$ day, were effected by upturning followed by the addition of PBS three times and not by centrifugation at 1600×g. Also on the 5$^{th}$ day, the supernatant was removed by upturning the plates.

Cell survival was determined by incubation with ST1926 for 24 hours, 48 hours after the removal of the compound. Incubation with the product for 24 hours was able to inhibit cell proliferation in a concentration dependent manner. Table 1 shows the IC50 values (concentration of product which inhibits cell survival by 50%), calculated for each tumour cell line studied. ST1926 has demonstrated a cytotoxicity greater than around 10 times towards the human promyelocytic leukaemia tumour cell line NB4 (IC50=0.022 μM) with respect to those calculated towards the other tumoral lines.

TABLE 1

Cellular cytotoxicity of ST1926

| Cell line | IC50 (μM) |
|---|---|
| Promyelocitic leukemia | |
| NB4 | 0.02 |
| HL-60 | 0.2 |
| Prostate carcinoma | |
| PC3 | 0.21 |
| DU145 | 0.10 |
| Colon carcinoma | |
| LoVo | 0.24 |
| Ovarian carcinoma | |
| A2780 | 0.10 |
| A2780/Dx | 0.20 |
| IGROV-1 | 0.23 |
| IGROV-1/Pt | 0.33 |
| Melanoma | |
| MeWo | 0.23 |
| MeS 2.21 | 0.23 |
| Glioblastoma | |
| GBM | 0.18 |
| Lung carcinoma | |
| A431 | 0.25 |
| NCI-H460 | 0.19 |
| Osteosarcoma | |
| SAOS | 0.25 |
| U2OS | 0.26 |

EXAMPLE 9

Evaluation of the Effect of ST1926 on the Tumoral Cell Cycle

To evaluate the effect of the compound according to the invention, on various phases of the cell cycle, cyto-fluorometric cell cycle analyses were performed.

HL60 or NB4 cells were seeded onto plates at a density of 150.000 cells/ml in RPMI 1640 medium containing 10% FCS, the test compound (ST 1926) was added, solubilised in 0.1% DMSO at concentrations of between 0.01 and 0.1 μM, in the presence or absence of sub-optimal doses of ATRA (5-10 nM for NB4 and 0.5 μM for HL60) in the dark and placed in an incubator for 3 days without changing the culture medium.

On the third day of treatment 500.000 cells were sampled, centrifuged at 180×g for 5 minutes, washed twice in calcium and magnesium free PBS. The cells (1×10⁶/ml of fixative) were fixed for at least 1 hour in a fixation mixture comprised of acetone/methanol 1:4 v/v maintained at −20° C. and 50% of calcium and magnesium free PBS; then the cells were centrifuged, washed in calcium and magnesium free PBS, and again centrifuged and washed. The cellular precipitate was incubated for 30 minutes in the dark at room temperature with 200 µl of propidium iodate (100 µg/ml) and 200 µL of RNAse (150 KU/mg).

The samples with filtered through nylon filters (60-80 µm diameter) and analysed by cyto-fluorimeter FACScan (Becton Dickinson), acquiring 20000 events/sample, at an excitation wavelength of 488 nm and emission wavelength of 620 nm. The analysis of the percentages of the cell cycle phases was performed using a dedicated software package, Modfit v. 2.0. (Becton Dickinson).

For the cell cycle analysis of prostate carcinoma cells PC3, the cells were seeded in plates at a density of 500000 cells/ml in RPMI medium. After treatment with compound ST1926 for 24 hours, cells were analysed as described above.

EXAMPLE 9/1

Evaluation of the Effect of ST1926 on the Cell Cycle of Human Promyelocytic Leukaemia NB4 Cells The analysis of the effect of treatment with ST1926 (for 3 days) on the cell cycle of NB4 has shown that the compound according to this invention at concentrations of 0.08 and 0.1 µM induces growth arrest in the duplication S phase of the cycle and apoptosis. The results obtained are reported in Table 2.

TABLE 2

Effect of ST1926 on the cell cycle of NB4

| TREATMENT | G0/G1 | S | G2 + M | APOPTOSIS |
|---|---|---|---|---|
| CONTROL | 53.4 | 35.5 | 11.1 | 26.6 |
| ST1926 0.01 µM | 48.4 | 38.8 | 12.8 | 19.9 |
| ST1926 0.02 µM | 48.2 | 39.4 | 12.4 | 28.4 |
| ST1926 0.04 µM | 51.3 | 35.7 | 13.0 | 33.9 |
| ST1926 0.08 µM | 41.4 | 53.6 | 5.0 | 45.0 |
| ST1926 0.1 µM | 50.6 | 46.1 | 3.3 | 53.6 |

EXAMPLE 9/2

Evaluation of the Effect of ST1926 on the Cell Cycle of Human Promyelocytic Leukaemia HL-60 Cells The analysis of the effect of the treatment with ST1926 on the cell cycle in HL-60 cells for three days of treatment shows that at a concentration of 0.5 and 1 µM, the cell cycle is not measurable, however, the compound has demonstrated a strong pro-apoptotic effect.

The results obtained are reported in Table 3.

TABLE 3

Effect of ST1926 on the cell cycle of human promyelocytic leukaemia HL-60 cells

| TREATMENT | G0/G1 | S | G2 + M | APOPTOSIS |
|---|---|---|---|---|
| CONTROL | 57.9 | 30.9 | 11.2 | 10.5 |
| ST1926 0.0025 µM | 54.9 | 33.4 | 11.7 | 8 |
| ST1926 0.005 µM | 53.4 | 34.4 | 12.2 | 14.0 |
| ST1926 0.01 µM | 52.0 | 35.4 | 12.6 | 12.5 |
| ST1926 0.05 µM | 45.0 | 42.0 | 13.0 | 13.0 |
| ST1926 0.1 µM | 39.9 | 46.8 | 13.3 | 27.5 |
| ST1926 0.5 µM | n.e. | n.e. | n.e. | 82 |
| ST1926 1 µM | n.e. | n.e. | n.e. | 86.5 |

EXAMPLE 9/3

Effect of ST1926 on the Cell Cycle of Prostate Carcinoma PC3 Cells

The analysis of the effect of treatment for 24 hours with ST1926 on the cell cycle of PC3 has shown that immediately at the end of the treatment, the compounds tested induced apoptosis at the highest concentration examined (0.4 µM); after 24 hours of cell recovery, the cells were accumulated in S phase, whilst at a concentration of 0.4 µM, cellular apoptosis was induced.

The results obtained are reported in Table 4.

TABLE 4

Effect of ST1926 on the cell cycle of human prostate carcinoma PC3 cells

| TREATMENT | G0/G1 | S | G2 + M | APOPTOSIS |
|---|---|---|---|---|
| 24 hours of treatment and 0 hours of recovery | | | | |
| CONTROL | 54.8 | 24.6 | 20.6 | 8 |
| ST1926 0.02 µM | 54.0 | 24.2 | 21.8 | 9 |
| ST1926 0.05 µM | 55.8 | 23.6 | 20.6 | 11 |
| ST1926 0.1 µM | 52.0 | 35.4 | 28.0 | 10 |
| ST1926 0.2 µM | n.v. | n.v. | n.v. | 13.5 |
| ST1926 0.4 µM | n.v. | n.v. | n.v. | 25 |
| 24 hours of treatment and 24 hours of recovery | | | | |
| CONTROL | 49.9 | 31.8 | 22.3 | 10.5 |
| ST1926 0.02 µM | 44.6 | 30.4 | 25.0 | 13 |
| ST1926 0.05 µM | 44.9 | 29.5 | 25.6 | 15 |
| ST1926 0.1 µM | 45.8 | 25.8 | 28.4 | 10 |
| ST1926 0.2 µM | 31.8 | 43.2 | 25.0 | 13 |
| ST1926 0.4 µM | n.e. | n.e. | n.e. | 26 |

Cytotoxic Activity in Vitro of ST1926 in Combination with TRAIL (Tumor Necrosis Factor-Related Apoptosis-Inducing Ligand)

Lymphocytes together with Natural Killer cells are responsible of TRAIL production (Tumor Necrosis Factor-related apoptosis-inducing ligand) a member of the TNF cytokine family (Tumor Necrosis Factor). This membrane protein induces apoptosis in a wide variety of transformed cells and unlike other members of this family, it does not seem to be cytotoxic to normal cells in vitro. TRAIL induces apoptosis by interacting with two death domain-containg death receptors DR4 and DR5. Therefore, TRAIL is considered to be a tumor-selective, apoptosis-inducing cytokine and a promising new candidate for cancer prevention and treatment (Neoplasia, 6:535-546, 2001).

A study of cytotoxicity of ST1926 in combination with TRAIL was performed in two different tumor cell lines such as M109 murine lung carcinoma and A2780/Dx multidrug-resistant human ovarian carcinoma. Cells were maintained in RPMI 1640 medium containing 10% FCS, 1% sodium pyruvate and 1% glutamine.

The cells were seeded in a volume of 250 µl in 96 well plates and incubated for 24 hours at 37° C. The following day, test compound ST 1926 [(2E)-3-[3'-(1-Adamantyl)-4'-hydroxy[1,1'-biphenyl]-4-yl]-2-propenoate/ic acid] or TRAIL were added at increasing concentrations, and the cells were incubated for a further 72 hours at 37° C. in a humidified atmosphere containing 5% $CO_2$. On the 5$^{th}$ day, the supernatant was removed by upturning the plates. 200 µl of PBS and 50 µl of cold, 80%. TCA were added. The plates were then left to incubate on ice for at least 1 hour. The TCA was removed by upturning; the plates were washed three times by immersion in distilled water and dried first on paper, then with a jet of hot air. To all wells were added 200 µl of 0.4% sulphorodamine B in 1% acetic acid. The plates were incubated at room temperature for a further 30 minutes. The sulphorodamine B was removed by upturning, the plates were washed by immersion in 1% acetic acid three times, then dried firstly with absorbent paper, then with a jet of hot air. 200 µl of 10 mM Tris base were added into all the wells and the plates were stirred for at least 20 min. The optical density was measured using a Multiskan spectrophotometer at 540 nm.

The interaction between ST1926 and TRAIL was determined by using the analysis of Drewinko et al. (Cancer Biochem. Biophys. 1: 187-195, 1976).

The analysis was performed as follows:
(SFa×SFb/Sfa+SFb)/100, where SFa was the survival fraction of ST1926 and SFb was the survival fraction of TRAIL.

Figure 2:
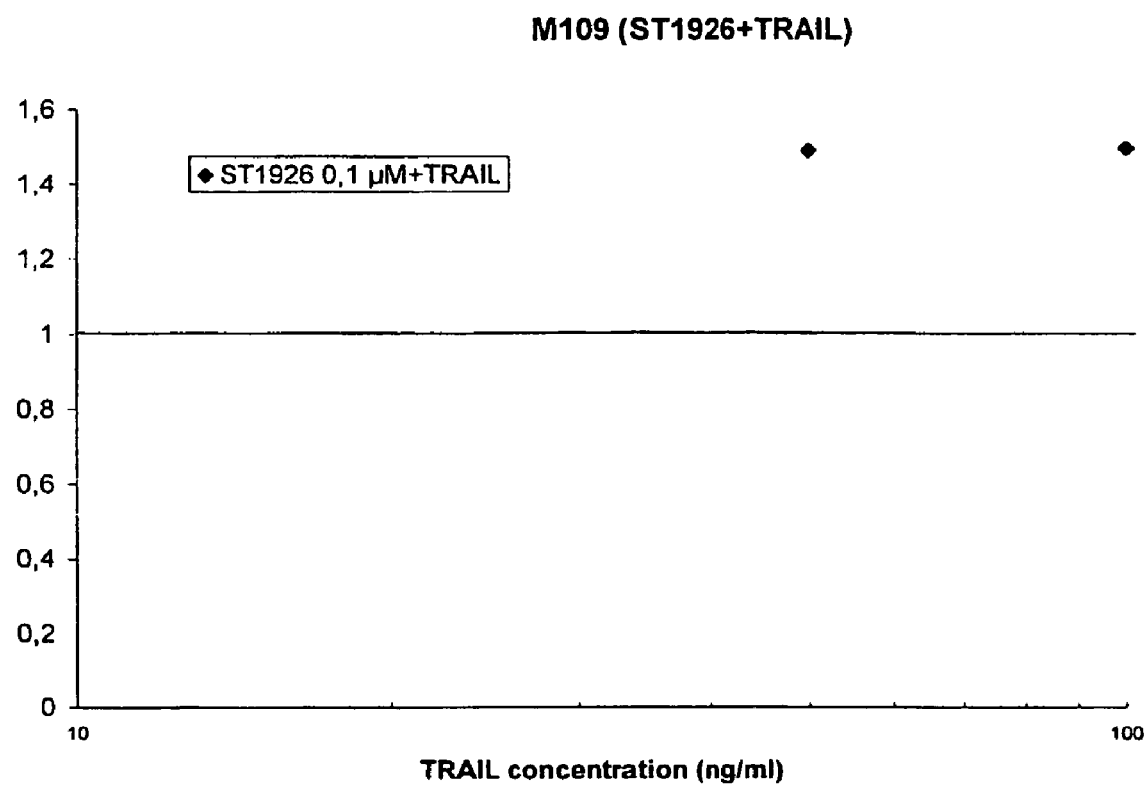

Values indicated the following effects:
A value>1 synergism, <1 antagonism, =1 no effect.
In both cell lines, ST1926 showed a synergic activity with TRAIL (FIGS. 1 and 2).

Antitumoral Activity of ST1926 in the Murine Pulmonary Carcinoma Models M109 and 3LL Murine pulmonary adenocarcinoma Madison 109 cells (M109) were maintained by s.c. passage of tumor fragments. The day of inoculation, the cell suspension was injected i.m. in the rear left limb of a 20 g male BALB/c mouse at a density of $3 \times 10^5$ cells/mouse. 3LL murine Lewis lung carcinoma was routinely maintained by i.m. passages (every 10-14 days) of $1 \times 10^5$ cells/mouse in C57BL/6J mice. For antitumor activity experiments, tumors were excised from donor mice and after mechanical desegregation and enzymatic digestion tumor cell viability was assessed by the trypan blue dye exclusion test. Then, $1 \times 10^5$ cells/100 µl/mouse were injected i.m. into the right hind leg muscle of C57BL/6J mice.
Tumor dimension measurements were performed using a digital calliper (Vernier Caliper) from the day in which the mass became measurable, twice weekly. The tumor mass was assessed from the size of the two principal dimensions (length and breadth), expressed in mm, applying the formula (length×breadth$^2$)/2 that is, the tumor volume in mm3. For every experimental group the percentage of inhibition of tumor volume (TVI%) was calculated, with respect to that of the control that is (100-(T/C%). TVI was evaluated 2 days after the final administration of ST1926.

The mean survival time (MST) was also measured and the increase in mean life-span expressed as ILS% (increase of life span) calculated as $(MST_T/MST_C) \times 100-100$.

The comparison between the values of TVI and of survival time, obtained for each group were performed with the non parametric Mann Whitney test for non paired data, using the Instat software from GraphPad inc.

The ST1926 solution was prepared immediately before use and solubilised in cremophor:ethanol 1:1 and subsquently diluted 1:4 in buffered saline solution. The treatments of the animals were carried out in a volume of 10 ml/kg. The treatment scheme for ST1926 at different doses was for 5 consecutive days (qdx5), beginning 1 day after the inoculation with the tumoral cells and was repeated for 3 cycles.

The mice (8 for each group) were weighed prior to each treatment, firstly, so as to be able to administer the correct quantity of substance, based on the eventual variations in weight observed throughout the period of drug administration, and also to be able to register the maximum weight loss throughout the treatment (BWL% max).

The results are reported in the following table 5. ST1926 demonstrated an increase in survival of animals with murine pulmonary tumors M109, at doses of 10 mg/kg, po and 15 mg/kg, i.p., according to the treatment protocol qdx5x3w and to inhibit tumor mass.

Moreover, ST1926 increased the life span of 3LL-tumor bearing mice at a dose of 10 mg/kg, p.o. and it decreased the tumor volume of 65%.

TABLE 5

Antitumoral activity of ST1926 (qdx5x3w) towards murine pulmonary M109 tumors

| Treatment | Dose (mg/kg) | BWL % Max | MST (range days) | ILS % | TVI % |
|---|---|---|---|---|---|
| M109 | | | | | |
| Control | / | 9 | 22 (13-34) | / | / |
| ST1926 | 10, i.p. | 9 | *28 (25-35) | 27 | 18 |
| ST1926 | 15, i.p. | 10 | **36 (30-42) | 64 | *46 |
| ST1926 | 10, p.o. | 10 | **35 (27-42) | 59 | *49 |
| 3LL | | | | | |
| Control | / | 3 | 21 (15-33) | / | / |
| ST1926 | 10, po | 7 | *32 (24-42) | 52 | ***65 |

*P < 0.05,
**P < 0.01,
***P < 0.001 vs. control (Mann-Whitney).

Antitumoral Activity of ST1926 in the Human Ovarian Carcinoma Models A2780 and A2780/Dx and Human no Small Cell Lung Carcinoma NCI-H460

The human ovarian carcinoma cells A2780, A2780/Dx and NCI-H460 were maintained in RPMI-1640 containing 10% FCS, 2 mM glutamine, 50 µg/ml gentamicin, at 37° C. in a humidified atmosphere containing 5% $CO_2$. The cells were trypsinised, collected in complete medium, centrifuged at approx. 1100 rpm for 10 minutes and the precipitate resuspended in Hank's 199 Medium; this operation was carried out twice. The cells were resuspended in Hank's 199 Medium at a density of $20 \times 10^6$/ml and 0.1 ml (equal to $2 \times 10^6$ cells/mouse) were injected s.c. into the right flank of CD1 nu/nu 6 week-old, female mice.

The ST1926 solution was prepared immediately before use and solubilised in cremophor:ethanol 1:1 and subsequently diluted 1:4 in buffered saline solution. The animal treatments were administered in a volume of 10 ml/kg. The treatment protocol for ST1926 at different doses was for 5 consecutive days (qdx5), beginning one day following tumor cell inoculation and repeated for 3 cycles.

Measurements of tumor dimensions were performed using a digital calliper (Vernier Caliper) twice weekly, from the time in which the mass was measurable. The tumor mass was evaluated from the size of the two principal dimensions (length and breadth), expressed in mm, applying the formula (length×breadth$^2$)/2, that is, the tumor volume in mm3. For each experimental group, the percentage of tumor volume inhibition was calculated (TVI%), with respect to the control, namely (100-(T/C%). TVI was evaluated 2 days after the final administration of ST1926.

The mice were measured until the control group tumors had reached a weight of 2 g, then the mice were sacrificed by cervical dislocation.

A comparison between the TVI values obtained for each group was performed using the non parametric Mann Whitney test for non-paired data, using the Instat software from GraphPad inc.

The mice were weighed prior to each treatment, firstly, so as to be able to administer the correct quantity of substance based on the possible changes in weight observed throughout the course of administration of the drug, and also to record the maximum weight loss throughout the treatment (BWL% max).

The results are reported in table 6. Also in this case ST1926 has inhibited tumor mass in mice with human ovarian adenocarcinoma A2780, multidrug-resistant A2780/Dx and human no small cell lung carcinoma NCI-H460 at doses ranging from 15 to 5 mg/kg, po according to the treatment protocol qdx5x3w.

TABLE 6

Antitumoral activity of ST1926 (qdx5x3w) towards human ovarian carcinoma A2780, A2780/Dx and no small cell lung carcinoma NCI-H460

| Treatment | Dose (mg/kg) | BWL % Max | Lethality | TVI % ± SE |
|---|---|---|---|---|
| A2780 | | | | |
| Control | / | 0 | 0/8 | / |
| ST1926 | 5, p.o. | 3 | 0/8 | *34 ± 8 |
| ST1926 | 10, p.o. | 5 | 0/8 | *39 ± 5 |
| A2780/Dx | | | | |
| Control | / | 0 | 0/8 | / |
| ST1926 | 10, po | 0 | 0/8 | *34 ± 3 |
| ST1926 | 15, po | 6 | 0/8 | *54 ± 9 |
| NCI-H460 | | | | |
| Control | / | | 0/8 | / |
| ST1926 | 15, po | 4 | 0/8 | *40 ± 2 |

*P < 0.05 vs. control.

ST1926 showed to be efficacious at the dose of 15 mg/kg, po according to the schedule qdx4x3w with and without Taxol (15 mg/kg, ip according to the schedule q7dx3) in NCI-H460 no small cell lung carcinoma (table 7).

TABLE 7

Antitumoral activity of ST1926 (qdx4x3w) towards no small cell lung carcinoma NCI-H460 with and without Taxol (q7dx3)

| Treatment | Dose (mg/kg) | BWL % max | Lethality | TVI % ± SE |
|---|---|---|---|---|
| Control | / | 3 | / | / |
| ST1926 | 15, po | 14 | 0/8 | **38 ± 8 |

TABLE 7-continued

Antitumoral activity of ST1926 (qdx4x3w) towards no small cell lung carcinoma NCI-H460 with and without Taxol (q7dx3)

| Treatment | Dose (mg/kg) | BWL % max | Lethality | TVI % ± SE |
|---|---|---|---|---|
| Taxol | 15, ip | 4 | 0/8 | 0 |
| 1926 + Tax | 15, po 15, ip | 16 | 0/8 | **°56 ± 6 |

**P < 0.01 vs control;
°P < 0.05 vs ST1926 (Mann-Whitney).

ST1926 showed a significant antitumor activity when administered at the dose of 15 mg/kg, p.o. according to the schedule qdx3x3w (table 8).

TABLE 8

Antitumoral activity of ST1926 (qdx3x3w) towards no small cell lung carcinoma NCI-H460

| Treatment | Dose (mg/kg) | BWL % max | Lethality | TVI % ± SE |
|---|---|---|---|---|
| Control | / | 3 | / | / |
| ST1926 | 15, po | 4 | 0/8 | *52 ± 7 |

*P < 0.05 vs control (Mann-Whitney).

Cytotoxicity of ST1879 Towards the Bovine Adrenal Gland Microcircle Endothelial (BMEC) Cell Line The endothelial cell line BMEC was used, previously prepared from fresh bovine adrenal glands in the following way. Glands were removed from the animals immediately following sacrifice and stored in ice until arrival in the laboratory. In sterile conditions (Bio-Hazard laminar flow hood), the glands were washed in a Betadine solution for 5 minutes and subsequently washed with 2 litres of sterile PBS. The glands were then cut into fragments, around 2 mm, with sterile disposable scalpels and transferred into polystyrene Falcon tubes containing PBS (30 ml per gland). After centrifugation at 600 rpm in a refrigerated centrifuge at 4° C., the supernatant was decanted. The pellet was resuspended in an equal volume (with respect to the volume of the precipitate) of collagenase A (Boehringer Mannheim) at 0.12% and incubated at 37° C. for 2 hours with agitation. Following successive filtration through filters (Sigma), firstly 200, and then 100 mesh, the supernatant was added to a solution of 15% DMEM FBS to inhibit the action of collagenase A. The solution was centrifuged at 1000 rpm at room temperature and the precipitate resuspended in DMEM medium containing 20% FBS, 50 µg/ml of bovine brain extract (BBE), 50 µg/ml of heparin (Sigma), 0.5% v/v gentamicin (Sigma), 1% v/v L-glutamine and seeded onto gelatinised Petri dishes with 1% of gelatine (porcine gelatine Sigma). On reaching confluence, the cells were characterised with endothelial markers, such as factor VIII.

Cytotoxicity tests were carried out using BMEC cells. The cells were seeded in a volume of 200 µl in 96 well plates and incubated for 24 hours at 37° C. The following day, test compound ST1879 was added, at decreasing concentrations from 200 µM to 1.56 µM. The cells were incubated for a further 24 hours at 37° C. in a humidified atmosphere containing 5% CO$_2$. On the 3rd day, the medium was removed by upturning the plates and the washes of the plates on the 3rd day were performed by upturning and adding 300 µl of PBS 4 times. After washing, 200 µl/well of the media used for plating on gelatine, previously described, were added. On the 5th day, the medium was removed by upturning the plates and the cells were treated with a solution of cold 15% TCA for 1 hour. The wells were washed three times with water by immersion of the plate and removal by upturning. To each well were added 200 µl of 0.4% sulphorodamine B in 1% acetic acid. The plates were incubated at room temperature for a further 30 minutes. The sulphorodamine B was removed by upturning, the plates were washed by immersion in 1% acetic acid three times, then were dried firstly on absorbent paper, then with a jet of hot air. To each well was added 200 µl of 10 mM Tris base and the plates were left with agitation for at least 20 minutes. The optical density was determined using a Multiskan spectrophotometer at 540 nm.

Cellular survival was determined by incubation with ST1879 for 24 hours and 48 hours after the removal of the compound. Incubation with the product for 24 hours was able to inhibit cellular proliferation in a concentration dependant manner. Table 5 shows the IC50 values (concentration of product which inhibits 50% of cellular survival), calculated. ST1879 has demonstrated poor cytotoxicity equal to 105 µM and a non toxic concentration equal to 25 µM which has been later used to study the effect of ST1879 on endothelial cell migration (see table 9).

TABLE 9

Cellular cytotoxicity of ST1879 towards endothelial cells

| Cell line | $IC_{50} \pm SD$ (µM) | $IC_0$ |
|---|---|---|
| BMEC | 105 ± 14 | 25 µM |

Endothelial BMEC Cells Chemotaxis

To evaluate the effect of ST1879 on endothelial cell chemotaxis, a Boyden chamber was used, consisting of a chamber with two wells, one under and the other above separated by a polycarbonate filter with a defined pore size of 8 µm. In the lower well was introduced the chemoattractant factor 1% FBS in DMEM, into the upper well, the bovine subrenal-microcircle endothelial cells (BMEC) were introduced, suspended in DMEM containing 1% fatty acid free porcine serum albumin. The capacity of ST1879 to inhibit cellular migration through the polycarbonate filter in the direction of the chemoattractant factor, was quantitatively evaluated by counting the number of cells present on the lower side of the filter. The percentages of migration reported in table 8 were calculated according to the formula: (treated−control/control)×100. ST1926 has shown inhibition of chemotaxis of the BMEC cells towards the chemoattractant stimulant FCS, at concentrations equal to 50 and 25 µM (table 10).

TABLE 10

Inhibition of the migration of BMEC cells induced by ST1879

| | % of inhibition of migration | |
|---|---|---|
| Cell line | 50 µM | 25 µM |
| BMEC | 91% (6.1 cells ± 2.4 vs 72.1 ± 7.4 cells in the Control) | 42.7% (41.3 cells ± 10.2 vs 72.1 ± 7.4 cells in the control) |

Effect of ST1879 on the Differentiation of HUVEC Cells on Matrigel

The differentiation assay of endothelial cells on matrigel, is an assay commonly used to evaluate the antiangiogenic activity of a product. Matrigel is a reconstituted basal membrane extract from tumours, consisting mainly of laminin and collagen IV, on which the endothelial cells organise in three dimensional structures similar to capillaries. The network intensity is measurable by the microscopic counting of "nodes" defined as the points of intersection where more than two tubular structures depart, or through a computerised imaging system able to calculate the percentage of area occupied by capillary structures.

Matrigel at 4° C. (Becton-Dickinson) was plated in 24 well plates and allowed to gellify at 37° C. in an incubator for 30 min. The human-umbilical-cord endothelial cells HUVEC (Clonetics) were resuspended in 500 µl of culture medium in the presence or absence of ST1879 at a non-toxic concentration of 25 µM and were plated on the matrigel. After 5 hours of incubation, the cells were fixed with a solution of 4% paraformaldehyde in PBS. The results were quantified by the microscopic count of the number of nodes/field for three independent fields and expressed as a percentage with respect to the positive control.

ST1879 has shown a 61% inhibition of differentiation of the endothelial cells on matrigel at a concentration of 25 µM (table 11).

TABLE 11

Inhibition of HUVEC cell differentiation induced by ST1879

| Cell line | % of inhibition of differentiation on matrigel |
|---|---|
| HUVEC | ST1879 (25 µM) = 61% (8.2 nodes vs 21.2 nodes in the control) |

Cellular Cytotoxicity of ST1879 and ST1898 Towards Human Tumoral Cell Lines

The human acute promyelocytic leukaemia cell line NB4 was used to carry out the cytotoxicity tests, maintained in RPMI 1640 containing 10% foetal calf serum (FCS) and 1% glutamine.

A further two solid tumour cell lines were also used:
1. Human prostate carcinoma PC3. This cell line was maintained in RPMI 1640 medium containing 10% FCS, 1% sodium pyruvate and 1% glutamine.
2. Human colon adenocarcinoma LoVo. This cell line was maintained in HAM's F-12 medium, containing 10% FCS and 1% glutamine.

Cytotoxicity tests were performed using 10000, NB4 cells/well. The cells were seeded in a volume of 250 µl in 96 well plates and incubated for 24 hours at 37° C. The following day the test compound ST 1879 was added at increasing concentrations, and the cells incubated for a further 24 hours at 37° C. in a humidified atmosphere containing 5% $CO_2$. On the $3^{rd}$ day, the medium was removed by centrifugation of the plate at 1600×g for 10 min and the supernatant decanted. 250 µl of PBS were added; then the plates were centrifuged again at 1600×g for 10 minutes and the supernatant decanted. 200 µl/well of RPMI 1640 medium containing 10% FCS were added, and the plates were incubated at 37° C. for a further 48 hours. On the $5^{th}$ day, the plates were again centrifuged at 1600×g for 10 minutes, and the medium was removed by upturning the plates, 200 µl of PBS and 50 µl of 80% cold TCA were added. The plates were then allowed to incubate in ice for at least an hour. The TCA was removed by upturning; the plates were washed three times by immersion in distilled water and dried, firstly with paper, then with a jet of hot air. Into each well were added 200 µl of 0.4% sulphorodamine B in 1% acetic acid. The plates were incubated at room temperature for a further 30 minutes. The sulphorodamine B was removed by upturning, the plates were washed by immersion 3 times in 1% acetic acid, then dried firstly on absorbent paper, then with a jet of hot air. Into each well were added 200 µl of 10 mM Tris base and the plates were stirred for at least 20 minutes. The optical density was measured using a Multiskan spectrophotometer at 540 nm.

For the adherent cell lines PC3-and LoVo, the procedure used was the same, whilst the washes of the plates on the $3^{rd}$ day, were performed by upturning and adding PBS three times and not by centrifugation at 1600×g. Also on the $5^{th}$ day, the supernatant was removed by upturning the plates.

Cellular survival was determined by incubation with ST1879 or ST1898 for 24 hours, and after 48 hours following removal of the compound. Incubation with the product for 48 hours was sufficient to inhibit cellular proliferation in a concentration dependent manner. Table 10 shows IC50 values (concentration of product which inhibits 50% of cellular survival), calculated for each tumoral cell line studied. ST1879 has demonstrated a greater cytotoxicity towards LoVo cells (IC50=5.2 µM) with respect to that calculated towards the prostate carcinoma line PC3 (IC50=13.6 µM) and towards the human promyelocytic NB4 line (58.5 µM). ST1898 has also shown to be more active towards colon carcinoma LoVo. (see table 12).

TABLE 12

Cellular cytotoxicity of ST1879 and ST1898

| Compound tested | Cell line | IC50 ± SD (µM) |
|---|---|---|
| ST1879 | NB4 | 58.5 ± 3.2 |
| ST1879 | PC3 | 13.6 ± 2.1 |
| ST1879 | LoVo | 5.2 ± 0.9 |
| ST1898 | NB4 | 8.8 ± 0.6 |
| ST1898 | PC3 | 1.7 ± 0.2 |
| ST1898 | LoVo | 0.38 ± 0.02 |

Pro-Differentiating Effects of ST1879 and ST189.8 on NB4 Cells

NB4 cells were plated at a density of 150000 cells/ml in RPMI 1640 medium containing 10% foetal serum. The cells were then treated with ST1879 or ST1898 at decreasing concentrations starting from 0.4 µM to 0.01 µM and placed in an incubator for three days without any change of the media. To measure the differentiating effect 500000 cells from each sample were collected, centrifuged and resuspended in 1 ml of RPMI 1640 medium containing 10% serum, 1 mg/ml nitroblue tetrazolium (NBT) and 100 ng of PMA (phorbol myristyl acetate). The cells, resuspended as above, were incubated at 37° C. for 60 minutes. At the conclusion of incubation the cells were centrifuged and the precipitate resuspended in 1 ml of PBS containing 10% Tritonx100. The samples were sonicated until lysed and then read by spectrophotometer at a wavelength of 540 nm. Samples containing differentiated cells turn a purplish colour whilst the control samples and/or these with non differentiated cells remain white or much less intensely coloured. The pro-differentiating action of ST1879 or of ST1898 has been evaluated in terms of AC50 (activating concentration for 50% cellular differentiation) as reported below. ST1898 has demonstrated having a good pro-differentiating capacity, measurable by an AC50 value equal to 19 nM (see table 13).

TABLE 13

Pro-differentiating effects of ST1879 and ST1898 on NB4 cells

| Product | AC50 (nM ± SD) |
|---|---|
| ST1879 | 55 ± 9 |
| ST1898 | 19 ± 0.8 |

Angiostatic Activity of ST1879, ST1926 and ST1898 in the Chicken Chorioallantoic Membrane (CAM) Model The chicken chorioallantoic membrane is a very vascularised membrane in which the vessels make their appearance at the 4th day of development, develop an arteriovenous system by the $8^{th}$ day of development, and actively proliferate until the $11^{th}$ day.

The aim of the study was to follow vasal development in the CAM under basal conditions and in the presence of an inducer bFGF (basic Fibroblast Growth Factor) of vasoproliferation. This study used chicken embryonal eggs at the initial stage of their development. On the $3^{rd}$ day of development an operation to open the shells was performed to make the vessels of the CAM visible. The treatment was administered on the $9^{th}$ day of development by applying a fragment of sterile gelatine (GELFOAM Pharmacia-Upjohn) about 1 mm³, to the CAM surface, onto which was administered the bFGF (50 ng/embryo) or the products in question, for 3 consecutive days.

The evaluation of the effect of the molecule on vasoproliferation was obtained by a comparison of the vessels at the time of zero treatment with these of later times (12th day).

The results are reported as follows in table 14. The three products demonstrated having angiostatic activity in the chicken chorioallantoic membrane model at concentrations of between 0.25 and 0.5 µg/embryo (table 14).

TABLE 14

Angiostatic activities of ST1879, ST1926, ST1898

| Treatment | Concentration (µg/embryo) | n | $9^{th}$ day (T0) | $12^{th}$ day (72 hours) | Δvessels |
|---|---|---|---|---|---|
| bFGF | 0.05 | 7 | 5 ± 1 | 19 ± 1 | 15 ± 1 |
| bFGF + 1879 | 0.05 + 0.5 | 6 | 4 ± 1 | 8 ± 1 | 4 ± 1 (−73%) |
| bFGF | 0.05 | 6 | 3 ± 1 | 22 ± 1 | 19 ± 1 |
| bFGF + 1926 | 0.05 + 0.25 | 8 | 3 ± 1 | 12 ± 2 | 9 ± 2 (−53%) |
| bFGF | 0.05 | 4 | 3 ± 1 | 28 ± 2 | 24 ± 1 |
| bFGF + 1898 | 0.05 + 0.25 | 6 | 3 ± 1 | 10 ± 1 | 7 ± 1 (−71%) |

Results are the mean ± SE of the number of vessels per sponge.

The invention claimed is:

1. A compound of Formula (I)

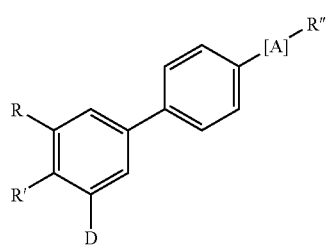

wherein:
R represents adamantyl wherein at least one of the CH can be substituted with C-halogen or C-alkyl and one of the $CH_2$ can be substituted by O, S, CH-halogen, CH-aryl, CH-heteroaryl, CH-arylalkyl, CH-heteroarylalkyl, CH-amino;
R' represents OR''', OCOR''', $COR^{IV}$;
R'-D represents O—$(CH_2)_n$—O; wherein n=1-3;
D represents H, OH, O-alkyl, $(CH_2)_n$—$NH_2$, $(CH_2)_n$—NH-alkyl, $(CH_2)_n$—OH, where n=1-4;
R'' represents tetrazole, $SO_3H$, $NHSO_3H$, CHO, COOH, COO-alkyl, CONHOH, CONH-aryl, CONH-$C_6H_4OH$, $CH_2OR'''$; $PO_3H_2$; CO—$(CH_2)_n$-aryl, where n=0-4;
R''' represents H, alkyl, aryl, arylalkyl, heteroaryl, heteroarylalkyl, $SO_3H$, α or β D- and L-glycosyl;
$R^{IV}$ represents H, OH, OR''';
(A) represents [C($R^V$, $R^{VI}$)—C($R^{VII}$, $R^{VIII}$)]n, [C($R^{IX}$)=C($R^X$)]n, [C≡C]n, where n=1-3;
$R^V$, $R^{VI}$, $R^{VII}$, $R^{VIII}$ represent H, alkyl, halogen, OH, OR'''; $NO_2$, $NH_2$, aryl, —O—, —$CH_2$—, $CX_2$— (where X is halogen), —CH(R''')—;
$R^{IX}$, $R^X$ represent H, OH, halogen, alkyl, aryl, CN, $NO_2$, COOR'''.

2. A pharmaceutical composition comprising a compound of claim 1 as an active ingredient and at least one pharmaceutically acceptable excipient and/or diluent.

3. A method of treating a pathology related to altered angiogenesis comprising administering to a subject an effective amount of a compound of claim 1, wherein the pathology is tumor metastatisation.

4. A method of treating a tumor comprising administering to a subject in need of same an effective amount of a compound of claim 1 having antitumoral activity.

5. The method according to claim 4, wherein the antitumoral activity is of cytotoxic nature.

6. The method according to claim 4, wherein the antitumoral activity is of apoptotic nature.

7. The method according to claim 4 in which the antitumoral activity is of antiangiogenic nature.

8. A method for the treatment of tumor metastasis comprising administering to a subject in need of same an effective amount of a compound of claim 1.

9. The method according to claim 8, wherein the tumor is selected from the group consisting of sarcoma, carcinoma, carcinoid, bone tumour, neuroendocrine tumour, lymphoid leukaemia, myeloid leukaemia, monocytic leukaemia, megakaryocytic leukaemia or Hodgkin's disease.

10. The method according to claim 9 in which the tumor is an acute promyelotic leukaemia.

11. A combination consisting of at least one compound of claim 1 with at least one anticancer drug.

12. The combination of claim 11, in which the anticancer drug is selected from the group consisting of alkylating agents, topoisomerase inhibitors, antitubulin agents, intercalating compounds, anti-metabolites, natural products such as vinca alkaloids, epipodophyllotoxins, antibiotics, enzymes, taxans, cyto differentiating compounds, phosphotyrosine kinase inhibitors such as Iressa or Glivec, TRAIL (tumor necrosis factor-related apoptosis inducing ligand), agonists of DR4 or DR5 receptors (sites of TRAIL), compounds for immunological antitumoral therapy, antitumoral vaccines, and interferon α, β, or γ.

13. A pharmaceutical composition comprising the combination of claim 11, and one or more excipients or pharmacologically acceptable vehicles.

14. A method for the treatment of a tumor comprising administering to a subject in need of same an effective amount of a compound of claim 1 together with an anticancer drug.

15. The method of claim 14 wherein the compound of claim 11 is present as coadjuvant of the anticancer drug.

16. A compound of Formula (I)

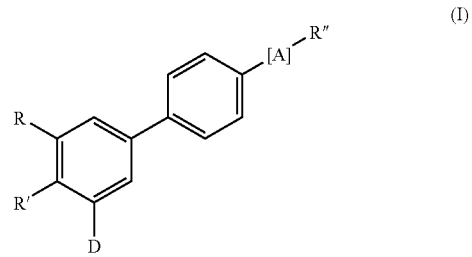

wherein:
R represents alkyl, cycloalkyl, heterocycloalkyl, phenyl, phenyl substituted, adamantyl wherein at least one of the CH can be substituted with C-halogen or C-alkyl and one of the $CH_2$ can be substituted by O, S, CH-halogen, CH-aryl, CH-heteroaryl, CH-arylalkyl, CH-heteroarylalkyl, CH-amino;
R' represents OR''', OCOR''', $COR^{IV}$;
R'-D represents O—$(CH_2)_n$—O; wherein n=1-3;
D represents H, OH, O-alkyl, $(CH_2)_n$—$NH_2$, $(CH_2)_n$—NH—alkyl, $(CH_2)_n$—OH, where n=1-4;
R'' represents tetrazole, $SO_3H$, $NHSO_3H$, CHO, COOH, COO-alkyl, CONHOH, CONH-aryl, CONH—$C_6H_4OH$, $CH_2OR'''$; $PO_3H_2$; CO—$(CH_2)_n$-aryl, where n=0-4;
R''' represents H, alkyl, aryl, arylalkyl, heteroaryl, heteroarylalkyl, $SO_3H$, α or β D- and L-glycosyl;
$R^{IV}$ represents H, OH, OR''';
(A) represents [C($R^V$, $R^{VI}$)—C($R^{VII}$, $R^{VIII}$)]n, [C($R^{IX}$)=C($R^X$)]n, [C≡C]n, where n=0-3;
$R^V$, $R^{VI}$, $R^{VII}$, $R^{VIII}$ represent H, alkyl, halogen, OH, OR'''; $NO_2$, $NH_2$, aryl, —O—, —$CH_2$—, $CX_2$— (where X is halogen), —CH(R''')—;
$R^{IX}$, $R^X$ represent H, OH, halogen, alkyl, aryl, CN, $NO_2$, COOR'''.

17. A compound having formula (I):

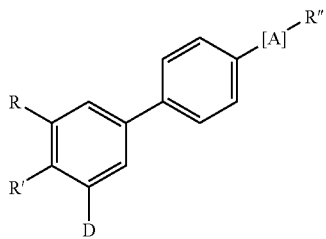

wherein R is adamantyl;
R' is OR''' or COR$^{IV}$;
D is H;
R''' is H, alkyl or aryl;
R$^{IV}$ is H, OH or OR''';
(A) is C(R$^{IX}$)=C(R$^{X}$) or C≡C;
R$^{IX}$ is H or halogen;
R$^{X}$ is H or halogen; and,
R'' is COOH, SO$_3$H, CONHOH, or PO$_3$H$_2$.

18. The compound of claim 17 wherein R' is hydroxy or —COOH.
19. The compound of claim 17 wherein R' is hydroxy.
20. The compound of claim 17 wherein R'' is —COOH.
21. The compound of claim 17 wherein R$^{IX}$ is H and R$^X$ is H.
22. The compound of claim 17 wherein (A)-R'' is C(H)=C(H)—C(=O)OH.
23. A method of treating cancer or tumours comprising contacting the cancer or tumour cells with a compound of claim 17 having antitumoral activity, wherein the cancer is prostate cancer, or leukemia.
24. The method of claim 23 wherein the leukemia is lymphoid leukemia, myeloid leukemia, monocytic leukaemia, megakaryocytic leukemia, or acute promyelotic leukaemia.
25. A method for inducing apoptosis or cell death comprising contacting target cells with a compound of claim 17, effective to induce apoptosis, or induce cell death in the target cells, wherein the target cells are prostate cancer, or leukemia cells.

* * * * *